US010653802B2

(12) United States Patent
Xu et al.

(10) Patent No.: US 10,653,802 B2
(45) Date of Patent: May 19, 2020

(54) PHOTOLUMINESCENT HYDROGEL

(71) Applicant: New Jersey Institute of Technology, Newark, NJ (US)

(72) Inventors: Xiaoyang Xu, Livingston, NJ (US); Yunghao Tsou, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 85 days.

(21) Appl. No.: 15/702,923

(22) Filed: Sep. 13, 2017

(65) Prior Publication Data
US 2018/0071409 A1    Mar. 15, 2018

Related U.S. Application Data

(60) Provisional application No. 62/394,383, filed on Sep. 14, 2016.

(51) Int. Cl.
| | |
|---|---|
| *A61K 49/00* | (2006.01) |
| *A61K 9/00* | (2006.01) |
| *C12P 17/14* | (2006.01) |
| *A61K 9/06* | (2006.01) |
| *C12P 11/00* | (2006.01) |
| *C08G 63/688* | (2006.01) |

(52) U.S. Cl.
CPC ........ *A61K 49/0073* (2013.01); *A61K 9/0024* (2013.01); *A61K 9/06* (2013.01); *A61K 49/0054* (2013.01); *A61K 49/0056* (2013.01); *C08G 63/6886* (2013.01); *C12P 11/00* (2013.01); *C12P 17/14* (2013.01); *C12Y 301/01003* (2013.01)

(58) Field of Classification Search
None
See application file for complete search history.

(56) References Cited

U.S. PATENT DOCUMENTS

| | | | | |
|---|---|---|---|---|
| 9,345,662 B2 * | 5/2016 | Sinko | ................... | A61K 9/0024 |
| 2008/0194708 A1 * | 8/2008 | Hossel | ................... | A61K 8/817 |
| | | | | 514/772.5 |

OTHER PUBLICATIONS

Yu et al., "Injectable hydrogels as unique biomedical materials", Chemical Society Reviews, 37(8), Aug. 2008, pp. 1473-1481.
Zhang, et al., "Design and performance of a sericin-alginate interpenetrating network hydrogel for cell and drug delivery", Scientific Reports, Jul. 5, 2015, p. 12374.
Zhang, et al., "Fluorescence imaging enabled urethane-doped citrate-based biodegradable elastomers", Biomaterials, 34(16), May 2013, pp. 4048-4056.
Annabi et al."25th Anniversary Article: Rational Design and Applications of Hydrogels in Regenerative Medicine", Advanced Materials, Jan. 2014, vol. 26, Issue 1, pp. 85-123.
Artzi, et al., "In vivo and in vitro tracking of erosion in biodegradable materials using non-invasive fluorescence imaging", Nature Materials, 10(9), Sep. 2011, pp. 704-709.
Berdichevski, et al., "Using bimodal MRI/fluorescence imaging to identify host angiogenic response to implants", Proceedings of the National Academy of Sciences of the United States of America, 112(16), Mar. 2015, pp. 5147-5152.
Bowman, et al., "Discovery of multiple hidden allosteric sites by combining Markov state models and experiments", Proceedings of the National Academy of Sciences of the United States of America, 112(9), Mar. 2015, pp. 2734-2739.
Breul, et al., "Fluorescent monomers as building blocks for dye labeled polymers: synthesis and application in energy conversion, biolabeling and sensors", Chemical Society Reviews, 42(12), Jun. 2013, pp. 5366-5407.
Bruchez et al. "Semiconductor nanocrystals as fluorescent biological labels", Science, Sep. 1998, vol. 281, No. 5385, pp. 2013-2016.
Bunzli, et al., "Taking advantage of luminescent lanthanide ions", Chemical Society Reviews, 34(12), Jun. 2005, pp. 1048-1077.
Chudakov et al., "Fluorescent proteins and their applications in imaging living cells and tissues", Physiological reviews, Jul. 2010, vol. 90, Issue 3, pp. 1103-1163.
Discher, et al., "Tissue cells feel and respond to the stiffness of their substrate", Science, 310(5751), Nov. 2005, pp. 1139-1143.
Elisseeff, et al., "Photoencapsulation of chondrocytes in poly(ethylene oxide)-based semi-interpenetrating networks", Journal of Biomedical Materials Research, 51(2), Aug. 2000, pp. 164-171.
Friend et al., "Electroluminescence in conjugated polymers", Nature, Jan. 1999, vol. 397, Issue 6715, pp. 121-128.
Ghobril, et al., "The chemistry and engineering of polymeric hydrogel adhesives for wound closure: a tutorial", Chemical Society Reviews, 44(7), Apr. 2015, pp. 1820-1835.
Giepmans et al., "The fluorescent toolbox for assessing protein location and function", Science, Apr. 2006, vol. 312, Issue 5771, pp. 217-224.
Grimsdale et al.,., "Synthesis of light-emitting conjugated polymers for applications in electroluminescent devices", Chemical reviews, Feb. 2009, 109(3), pp. 897-1091.
Gupta, et al., "Hydrogels: from controlled release to pH-responsive drug delivery", Drug Discov Today, vol. 7, Issue 10, May 2002, pp. 569-579.

(Continued)

*Primary Examiner* — James W Rogers
(74) *Attorney, Agent, or Firm* — Lerner, David, Littenberg, Krumholz & Mentlik, LLP

(57) ABSTRACT

Shown and described is a composition and a method to prepare a dopant-free photoluminescent hydrogel with synthetic polymers are disclosed. The hydrogel can be synthesized in one embodiment by incorporating an amino acid to a citric acid based polyester oligomer followed by multiple crosslinking group functionalization through a transesterification reaction using an enzyme such as *Candida antarctica* Lipase B (CALB) as a catalyst. The hydrogels are injectable, degradable, and their mechanical and photoluminescent properties are tunable. An in vivo study shows that the hydrogel emits strong fluorescence under visible light excitation and can completely degrade over time.

6 Claims, 14 Drawing Sheets

(13 of 14 Drawing Sheet(s) Filed in Color)

(56) References Cited

OTHER PUBLICATIONS

Gyawali, et al., "Fluorescence imaging enabled biodegradable photostable polymeric micelles", Advanced Healthcare Materials, 3(2), Aug. 2013, pp. 182-186.
Hardman, "A toxicologic review of quantum dots: toxicity depends on physicochemical and environmental factors", Environmental Health Perspectives, 114(2), Feb. 2006, pp. 165-172.
Hoffman, "Hydrogels for biomedical applications", Adv Drug Deliv Rev, vol. 64, Dec. 2012, pp. 18-23.
Jaiswal, et al., "Long-term multiple color imaging of live cells using quantum dot bioconjugates", Nature Biotechnology, 21(1), Dec. 2002, pp. 47-51.
Jeong, et al., "Biodegradable block copolymers as injectable drug-delivery systems", Nature, 388(6645), Aug. 1997, pp. 860-862.
Jiang, "Gelation Time and Rheological Property of Gelatin Gels Prepared with a Phosphate-buffered Saline-ethanol Solution", Case Western Reserve University, 2015.
Jiang, et al. "Rheology of highly swollen chitosan/polyacrylate hydrogels", Polymer, vol. 40, Issue 16, Jul. 1999, pp. 4593-4602.
Kim, et al., "Near-infrared fluorescence imaging for noninvasive trafficking of scaffold degradation", Scientific Reports, vol. 3, Feb. 2013, p. 1198.
Kremers et al., "Fluorescent proteins at a glance", Journal of cell science, Jan. 2011, vol. 124, Issue 2, pp. 157-160.
Kretlow, et al., "Injectable biomaterials for regenerating complex craniofacial tissues", Advanced Materials, 21(32-33), Apr. 2009, pp. 3368-3393.
Kwon, et al., "In vivo osteogenic differentiation of human turbinate mesenchymal stem cells in an injectable in situ-forming hydrogel", Biomaterials, vol. 35, Issue 20, Jul. 2014, pp. 5337-5346.
Li, et al., "Highly Photoluminescent CdTe/Poly(N-isopropylacrylamide) Temperature-Sensitive Gels", Advanced Materials, 17(2), Jan. 2005, pp. 163-166.
Li, et al., "Injectable and biodegradable hydrogels: gelation, biodegradation and biomedical applications", Chemical Society Reviews, 41(6), Nov. 2011, pp. 2193-2221.
Miyawaki et al., "Proteins on the move: insights gained from fluorescent protein technologies", Nature Reviews Molecular Cell Biology, Sep. 2011, 12(10), pp. 656-668.
Montgomery, et al., "Cell-penetrating metal complex optical probes: targeted and responsive systems based on lanthanide luminescence", Accounts of Chemical Research, 42(7), Feb. 2009, pp. 925-937.
Murphy et al., "Materials as stem cell regulators", Nature materials, 13(6), Jun. 2014, pp. 547-557.
Nienhaus et al., "Fluorescent proteins for live-cell imaging with super-resolution", Chemical Society Reviews, Feb. 2014, 43(4), pp. 1088-1106.

Perale, et al., "Hydrogels in spinal cord injury repair strategies", ACS chemical neuroscience, vol. 2, Issue 7, Jul. 2011, pp. 336-345.
Phelps et al., "Maleimide cross-linked bioactive PEG hydrogel exhibits improved reaction kinetics and cross-linking for cell encapsulation and in situ delivery", Advanced Materials, 24(1), Jan. 2012, pp. 64-70.
Ren, et al., "Injectable glycopolypeptide hydrogels as biomimetic scaffolds for cartilage tissue engineering", Biomaterials, vol. 51, May 2015, pp. 238-249.
Resch-Genger et al, "Quantum dots versus organic dyes as fluorescent labels", Nature methods, Sep. 2008, 5 (9), pp. 763-775.
Seliktar, "Designing Cell-Compatible Hydrogels for Biomedical Applications", Science, 336.6085, Jun. 2012, pp. 1124-1128.
Slaughter, et al., "Hydrogels in Regenerative Medicine", Advanced Materials, 21(32-33), Jul. 2009, pp. 3307-3329.
Thiele et al., "25th anniversary article: Designer hydrogels for cell cultures: a materials selection guide", Adv Mater, 26 (1), Nov. 2014, pp. 125-147.
Tsou, et al., "Hydrogel as a bioactive material to regulate stem cell fate", Bioactive Materials, vol. 1, Issue 1, Sep. 2016, pp. 39-55.
Veiseh et al., "Size- and shape-dependent foreign body immune response to materials implanted in rodents and non-human primates", Nature Materials, Jun. 2015, vol. 14, Issue 6, pp. 643-651.
Vo, et al., "Strategies for controlled delivery of growth factors and cells for bone regeneration", Advanced Drug Delivery Reviews, vol. 64, Issue 12, Sep. 2012, pp. 1292-1309.
Wang, et al., "Exploring natural silk protein sericin for regenerative medicine: an injectable, photoluminescent, cell-adhesive 3D hydrogel", Scientific Reports, vol. 4, Nov. 2014, p. 7064.
Wang, et al., "Therapeutic cell delivery and fate control in hydrogels and hydrogel hybrids", Advanced drug delivery reviews, vol. 62, Issues 7-8, Jun. 2010, pp. 699-710.
Wang, et al., "Tough photoluminescent hydrogels doped with lanthanide", Macromolecular rapid communications, 36 (5), Jan. 2015, pp. 465-471.
Watson, et al., "Biodegradable, phosphate-containing, dual-gelling macromers for cellular delivery in bone tissue engineering", Biomaterials, vol. 66, Oct. 2015, pp. 286-296.
Williams et al., "Relative fluorescence quantum yields using a computer-controlled luminescence spectrometer", Analyst, 108(1290), 1983, pp. 1067-1071.
Xie, et al., "Development of intrinsically photoluminescent and photostable polylactones", Advanced Materials, 26(26), Mar. 2014, pp. 4491-4496.
Yang, et al., "Development of aliphatic biodegradable photoluminescent polymers", Proceedings of the National Academy of Sciences of the United States of America, 106(25), Jan. 2009, pp. 10086-10091.
Yanushevich et al., "A strategy for the generation of non-aggregating mutants of Anthozoa fluorescent proteins", FEBS Letters, Jan. 2002, vol. 511, Issues 1-3, pp. 11-14.

\* cited by examiner

PHOTOLUMINESCENT HYDROGEL

CROSS-REFERENCE TO RELATED APPLICATION

The present application claims the benefit of the filing date of U.S. Provisional Patent Application No. 62/394,383, filed Sep. 14, 2016, the disclosure of which is hereby incorporated herein by reference.

FIELD OF USE

The present disclosure relates to a photoluminescent hydrogel. In particular, the present disclosure relates to a biodegradable and intrinsically photoluminescent hydrogel.

BACKGROUND

Hydrogels are cross-linked polymeric structures with dynamic swelling behavior in water. In particular, hydrogels are three-dimensional polymeric networks formed from hydrophilic homopolymers, copolymers, or macromers crosslinked to form insoluble polymer matrices, that can retain large amounts of water[1].

Due to their unique biocompatibility, compliant elasticity, flexible methods of synthesis, range of constituents, and desirable physic-characteristics, hydrogels have been the material of choice for many biomedical applications[2, 3, 4, 5]. Injectable hydrogels can be administered via minimally invasive procedures and appropriately fill irregular-shaped defects by acting as three-dimensional scaffolds. Injectable hydrogels have received much attention due to their potential biomedical and biological applications in the fields of imaging, biosensing, drug delivery tissue engineering, and regenerative medicine[6, 7, 8, 9, 10, 11, 12, 13, 14, 15]. Recently, there is an increasing demand for the development of biodegradable hydrogels endowed with fluorescent imaging moieties to further enhance the functions of the materials[16, 17].

Conventionally, synthetic hydrogels with photoluminescent properties can be prepared by conjugating or doping hydrogel matrix with fluorescent moieties such as organic dye, fluorescent protein, colloidal semiconductor nanocrystal, metal-ligand complex and lanthanide ions[19, 20, 21, 22, 23, 24]. However, among them, organic dye and fluorescent protein are subjected to certain limitations such as photo-bleaching and cellular toxicity[25, 26]. Semiconductor nanocrystals also pose risks to human health and the environment under certain conditions[27]. Similarly, toxicity from the heavy metal contents of metal-ligand complex and lanthanide ion imaging probes evokes significant safety concern for their biomedical applications especially for their long-term use in vivo[28].

Recently, the attempt to fabricate an injectable hydrogel by using silk protein sericin has been explored[19]. The gel is found to exhibit photoluminescence due to the intrinsic auto-fluorescence of sericin polypeptide. Nevertheless, the low quantum efficiency, untunable fluorescence property, eliciting immune response and the use of toxic glutaraldehyde as the cross-linker raise concerns for its biomedical applications.

Very recently, the development of a biodegradable polymer with potential biomedical application as an implanted elastomer and drug-loaded nanoparticle has been reported[29, 30, 31]. This newly developed biodegradable polymer displays superior biocompatibility both in vitro and in vivo, relative high quantum yields, photobleaching resistance, and tunable emission up to near infrared wavelengths and thus has potential biomedical applications, such as drug delivery nano-carriers and implanted scaffolds. However, the efforts to fabricate a hydrogel were unsuccessful due to the lack of functional cross-linking reactive moieties on the oligomers to form hydrogels.

Thus there still remains a need for a composition and method of preparing a hydrogel that contains both self-fluorescence and biodegradable characteristics without the above drawbacks. Furthermore there also remains a need in the art for a composition and method of preparing a hydrogel with the above properties that avoids eliciting an immune response and contributing to potential cytotoxicity and carcinogenesis.

SUMMARY OF THE INVENTION

The present disclosure solves the problems of current state of the art and provides many more benefits. Disclosed is a composition and method for a hydrogel that contains both self-fluorescence and biodegradable characteristics without the above drawbacks. Shown and described is a novel polyester-based biodegradable photoluminescence hydrogel-citric acid, hexaethylene glycol photoluminescent oligomer-ethyl thioglycolate (CHPO-ET)/polyethylene glycol (PEG) (CHPO-ET/PEG), via *Candida antarctica* lipase B (CALB) as a catalyst.

Synthesis of CHPO-ET/PEG included a method using biocompatible monomers including, but not limited to, hexa-ethylene glycol, citric acid, serine, and ethyl thioglycolate. It possesses tunable gel formation time by using various concentration, temperature and pH values. Moreover, in vivo study indicated that injectable CHPO-Ser-ET/PEG hydrogel emits fluorescence under gel image system at excitation 488 nm; emission 525 nm indicates the CHPO-Ser-ET/PEG hydrogel is a material, which contains injectable and easily tracked qualities under visible wavelength. The synthesized CHPO-ET/PEG hydrogel has benefits and utility as an auto-florescence, injectable biomaterial for drug delivery, and bio-imaging application, among other things.

In accordance with some of the embodiments of the present disclosure, a system and a method for preparing a hydrogel is disclosed. In one embodiment, biocompatible starting chemicals, such as citric acid, a diol molecule exampled by poly(ethylene glycol)-diol and amino acids, are employed. In another embodiment, an amino acid is developed that contains a polyester based hydrogel with degradable, injectable, and photoluminescent properties.

One objective of the present disclosure was to develop an amino acid containing, citric acid and a diol molecule such as polyethylene glycol (PEG) based polyester hydrogel, which is biodegradable, biocompatible, injectable and photoluminescent, enabling bio-imaging and in vivo implant tracking. The following, H1, C13 NMR and FTIR demonstrated the chemical synthesis successfully. Both synthesized CHPO-Cys-ET and CHPO-Ser-ET hydrogel showed strong emitted fluorescence as shown using spectrum devices. Also, the dynamic gelation time and gel strength applied by dynamic rheometer (DHR-III Discovery Hybrid Rheometer, TA Instruments) showed favorable results of the invention. The tunable gelation time, depending on the embodiment, was between 1~300 seconds that was exhibited in different formulations and the highest yield stress approximately ~10 kPa was found. When tested, in vivo, hydrogels not only succeeded in the injection test using nude mice but also emitted strong fluorescent under excitation 488 nm and emission can be up to 720 nm.

Photoluminescent hydrogels that function as both injectable scaffolds and fluorescent imaging probes hold great potential biomedical applications in drug delivery and tissue engineering. Unfortunately, current fluorescent hydrogels are fabricated by either conjugating or doping a fluorescent dye, fluorescent protein, lanthanide chelate or quantum dot into polymeric hydrogel matrix. Their biomedical applications have been severely limited by drawbacks such as photostability, carcinogenesis and toxicity associated with the above-mentioned dopants.

The present disclosure relates to a dopant-free photoluminescent hydrogel with synthetic polymers, which can be synthesized in one embodiment by incorporating an amino acid to a citric acid based polyester oligomer followed by multiple crosslinking group functionalization through a transesterification reaction using Candida antarctica Lipase B (CALB) as a catalyst.

The hydrogels are injectable, degradable, and their mechanical and photoluminescent properties are tunable. An in vivo study shows that the hydrogel emits strong fluorescence under visible light excitation and can completely degrade over time.

The above objects and other objects are met by the present invention. In addition the above and yet other objects and advantages of the present invention will become apparent from the hereinafter-set forth Brief Description of the Drawings, Detailed Description of the Invention and claims appended herewith.

Any combination and/or permutation of the embodiments are envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

To assist those of skill in the art in making and using the disclosed photoluminescent hydrogel and associated systems and methods, reference is made to the accompanying figures, wherein.

DETAILED DESCRIPTION

Figures 1A, 1B:
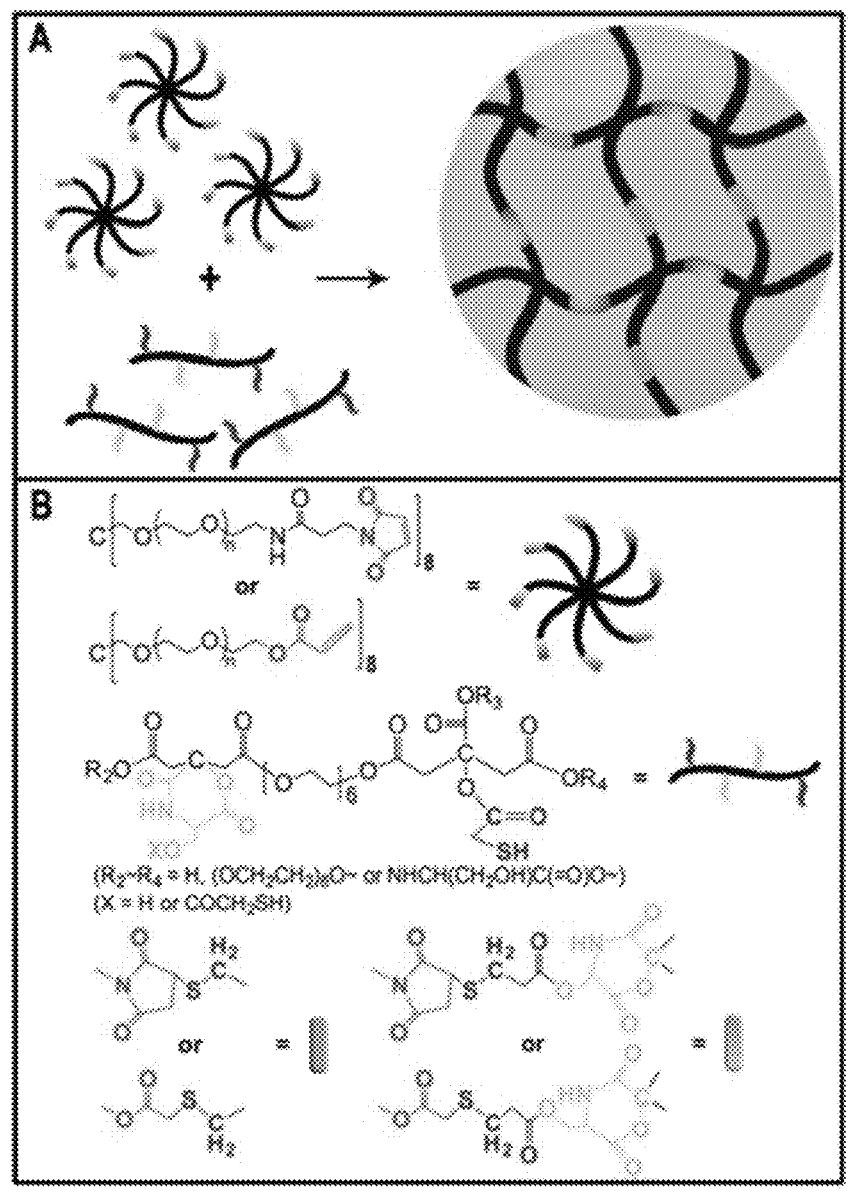
FIGS. 1A-1B illustrate a schematic demonstration of hydrogel formation in situ through cross-linking thiolated photoluminescent polyester and multi-arm functionalized PEG via Michael-addition reactions (A); and chemical structures of the cross-linking polymers (B), in accordance with one embodiment of the present disclosure.

In general, this disclosure overcomes the disadvantages of past attempts. Shown is a novel class of polyester based hydrogels, with degradable, injectable and self-fluorescent properties. In one embodiment, the hydrogel was successful developed through transesterification reaction using *Candida antarctica* Lipase B (CALB) as a catalyst.

One hurdle overcome was the issue of photoluminescent properties for a hydrogel. Conventionally, synthetic hydrogels with photoluminescent properties can be prepared by conjugating or doping hydrogel matrix with fluorescent moieties such as organic dye, fluorescent protein, colloidal semiconductor nanocrystal, metal-ligand complex and lanthanide ions. However, among them, organic dye and fluorescent protein are subjected to certain limitations such as photo-bleaching and cellular toxicity. Semiconductor nanocrystals also pose risks to human health and the environment under certain conditions. Similarly, toxicity from the heavy metal contents of metal-ligand complex and lanthanide ion imaging probes evoke significant safety concern for their biomedical applications especially for their long-term use in vivo.

The solution addressed in one embodiment is by the use of intrinsic photoluminescent oligomers. A photoluminescent oligomer used in the present disclosure was mainly composed by biocompatible materials such as citric acid, low molecular weight poly (ethylene glycol) diol, and amino acid. In order to introduce the photoluminescent property into the citric acid/PEG diol pre-polymer, an amino acid can be conjugated to the side chain of the citric acid/PEG diol pre-polymer. The oligomer successfully addressed the photoluminescent property.

A second issue addressed in the present disclosure was the hydrogel fabrication itself. Efforts to fabricate a hydrogel were challenging due to insufficiency of functional cross-linking molecules on the oligomers to form hydrogels. In addition, due to the low degree of polycondensation reaction (average molecular weight ~1,400), only 1-2 thiol functional groups can be incorporated into the oligomers when cysteine (CYS) was used for the purpose of introducing thiol functional groups.

One solution used in the present disclosure to address the second issue was introducing CALB biocatalyst. CALB-biocatalyst has successfully been applied over the last two decades especially in transesterification, however not to our knowledge in the present context. Michael addition can also be performed under mild conditions using CALB as a catalyst. Hence, CALB was introduced as a biocatalyst in transesterification reaction between oligomers and thiol contain compound. The 1H, 13C NMR, FTIR and Ellman's reagent tests demonstrated thiol contain compound successful conjugated on the backbone of the oligomers.

Depending on the implementation, briefly the innovation performs as follows. A more detailed explanation also follows herein. Regarding synthesis of the amino acid containing citric acid and hexaethylene glycol based polyester oligomers (CHPO-Ser), for synthesis of CHPO-Ser, equimolar amounts of citric acid (1.99 g) and hexaethylene glycol (2.13 g) were added to a 100 mL two-neck round bottom flask for ~180 mins reaction time at 155° C. under nitrogen protection. The reaction was placed on a magnetic stirrer, followed by the addition of serine (0.22 g) at a molar ratio 1:0.2 between citric acid and serine (Ser) for an 80 mins reaction time. The oligomers were cool at room temperature before dissolved in deionized (DI) water, then the products were purified by using a dialysis method (500~1 KD) and followed by freeze dryer for 3 days. The yield of CHPO-Ser oligomers were approach 82%. For the enzyme catalyzed CHPO-Ser and CHPO-Cys thiolation, in order to test whether it is possible to introduce multiple valences into the backbone of the amino acids containing CHPO-Ser through an enzyme catalyzed transesterification reaction, *Candida antarctica* Lipase B (CALB) was used as a catalyst to functionalize a thiol containing compound ethyl thioglycolate (ET) to CHPO-Ser. Oligomers were first dissolved in acetonitrile, ethyl thioglycolate and CALB (500 mg) was added in the solution (molar ratio of ethyl thioglycolate and citric acid=2.2:1) at 55~60° C., under magnetic stir and nitrogen protection for 7 hours. The reaction will stop via filtering out of CALB. The resultant thiol modified oligomers CHPO-Ser-ET was purified through dialysis by using a dialysis tubing (1 KD) and then followed by freeze dryer for 3 days. The yield of CHPO-Ser-ET oligomers were approach 73%. For photoluminescent CHPO-Ser-ET-PEG and CHPO-Cys-ET-PEG hydrogel fabrication: maleimide or acrylate functionalized multi-arm (4 arm or 8 arm) PEG (molecules weight 10 KDa) as choice for cross-linking agents. Gel can be formed through a maleimide-thiol conjugate addition or an acrylate-thiol Michael addition between synthesized photoluminescent oligomers and the above multivalent PEG macromolecules. Briefly, CHPO-Ser-ET or CHPO-Cys-ET and 4 or 8 arms PEG-Maleimide (MW 10 kDa) were dissolved individually in 1× PBS (PH=7.4 or 8) to form pre-gel solutions with predetermined weight concentrations from 2%-10%. By mixing two solutions, hydrogels can be formed between 1 second to half hour depends on the formulation at physiological conditions. In addition, the hydrogels are injectable and moldable and showed bright photoluminescent properties under UV or visible light excitation. A tilting vial method is also used to prove the formation of photoluminescent hydrogels.

The photoluminescent property of CHPO-Ser-ET/PEG hydrogel enables in vivo bioimaging. CHPO-Ser-ET/PEG and CHPO-Cys-ET/PEG hydrogel in small test tubes were first examined by using a gel imaging system. Only CHPO-Ser-ET/PEG hydrogel exhibited photoluminescence when exposed to light of wavelengths at 488 nm. Next, injected was the CHPO-Ser-ET/PEG hydrogel beneath the skin, into the nude mouse muscle tissue by using a dual-barrel syringe. Gel was formed in situ and the gelation was confirmed by sacrificing the mouse. The CHPO-Ser-ET/PEG hydrogel was readily detected and visualized under 488 nm excitation and 525 nm emission in vivo using a Syngene PXi imaging system (Synoptics Ltd). However, no fluorescence was detected for injected CHPO-Cys-ET/PEG hydrogel in vivo. No fluorescence was detected and the gel bump was disappeared within three weeks, indicating the in vivo degradation of the CHPO-Ser-ET/PEG hydrogel. These results clearly show that CHPO-Ser-ET/PEG hydrogel can be injected in vivo and optically detected and tracked without any fluorescence dye/labeling, suggesting the use this disclosed hydrogel as a implanted scaffold for bioimaging and in vivo material degradation tracking, among other things.

Adverting to the figures, FIGS. 1A-1B show a schematic of a hydrogel preparation approach by using biocompatible starting chemicals including citric acid, poly(ethylene glycol)-diol and amino acids. It will be understood that other starting chemicals could be employed. First, a series of biodegradable synthetic polymers can be synthesized from the above-mentioned monomers via a facile polycondensation reaction in one embodiment. A 6-membered ring chromophore can be formed through the amidation reaction between the unreacted carboxylic acid on the citrate and the N terminus of an amino acid, followed by an esterification reaction between the free carboxylic acid of the amino acid molecule and the hydroxyl group remaining on citrate. The ring contributes strong photoluminescent emitting due to the electrons hyperconjugation over the ring. The polyester oligomer can be further modified with multi-thiol functional groups through a high efficient CALB enzyme assisted transesterification reaction, introducing valences and facilitate the hydrogel formation through chemical cross-linking when combined with multi-arm polyethylene glycol (PEG) acrylates or maleimides, as shown in FIGS. 1A-1B.

A series of biodegradable photoluminescent hydrogels are described, which not only contains self-fluorescent property, but also possess tunable mechanical character and physiochemical properties. The effects of hydrogel formulation on gel degradation as well as model biomolecule drugs release were investigated. Those hydrogels show strong and tunable fluorescent emissions from blue to red and good in vitro cellular biocompatibility. In vivo fluorescence imaging of the injectable hydrogel has been conducted to demonstrate its potential biomedical applications as implants, drug delivery devices and imaging probes.

Characterization of the CHPO-Ser-ET

The materials and the methods of the present disclosure used in one embodiment will be described below. While the embodiment discusses the use of specific compounds and materials, it is understood that the present disclosure could employ other suitable materials. Similar quantities or measurements may be substituted without altering the method embodied below.

Figure 7:
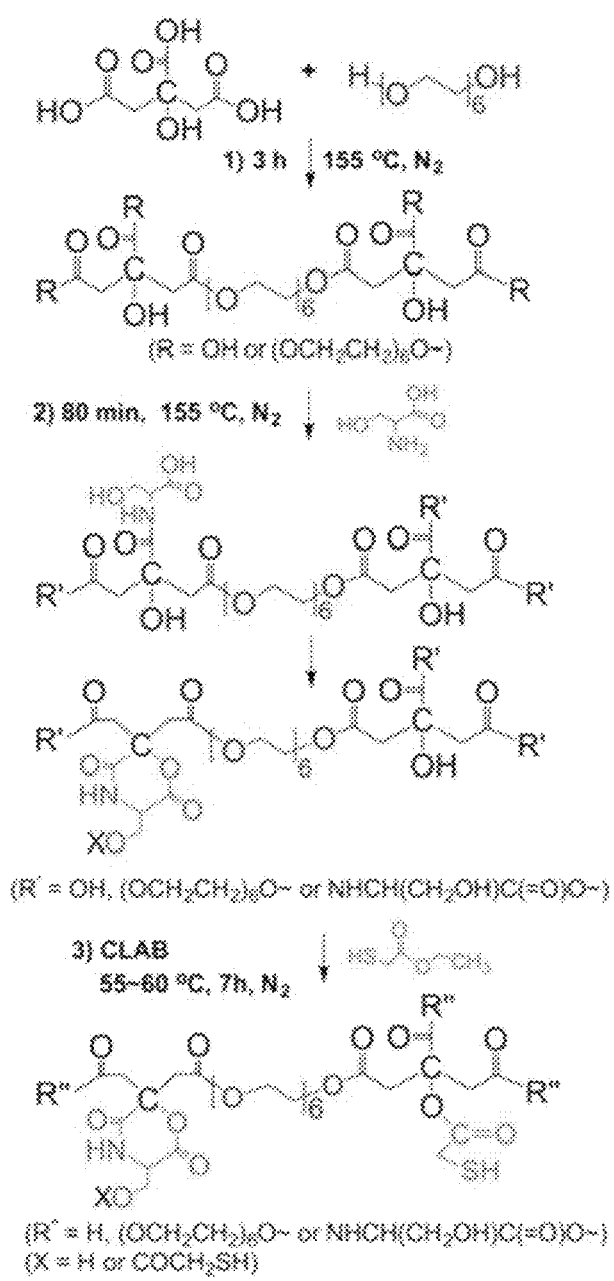
FIG. 7 is a schematic illustration of biodegradable photoluminescent (CHPO-Ser-ET) synthesis.

The proposed oligomer structures are shown in FIG. 7 (S1). FTIR spectroscopy of the CHPO-Ser was carried out using a Digilab FTS 3100 instrument. The FTIR spectra confirmed the presence of —SH at 2,560 $cm^{-1}$, —C(=O)NH— at 1,653 $cm^{-1}$, —$CH_2$— at 2,887 $cm^{-1}$ and —C=O at 1,735 $cm^{-1}$ FIG. 8A (S2-A). The average molecular mass of CHPO-Ser-ET measured by MALDI-TOF-MS was ~1,272 Da (FIG. 8B (S2-B)). Nuclear magnetic resonance (NMR) spectroscopy characterizations were recorded on a Bruker 500 MHz NMR spectrometer. In the $^1$H NMR spectra of CHPO-Ser: $^1$H (500 MHz, $CDCl_3$, δ) the presence of the peaks at 4.29 and 3.66 ppm (—$OCH_2CH_2$— from Hexaethlyene glycol), 2.88 and 2.95 ppm (—$CH_2$— from citric acid), 3.31 and 2.07 ppm from —$CH_2$— of —$CH_2SH$ and —SH respectively, confirmed the incorporation of thiol moieties into oligomer FIG. 8C-8D (S2-C, D). To verify that the ring structure exists on the oligomer chain, the $^{13}$C (500 MHz, $CDCl_3$, δ) was obtained.

Figures 9A, 9B, 9C:
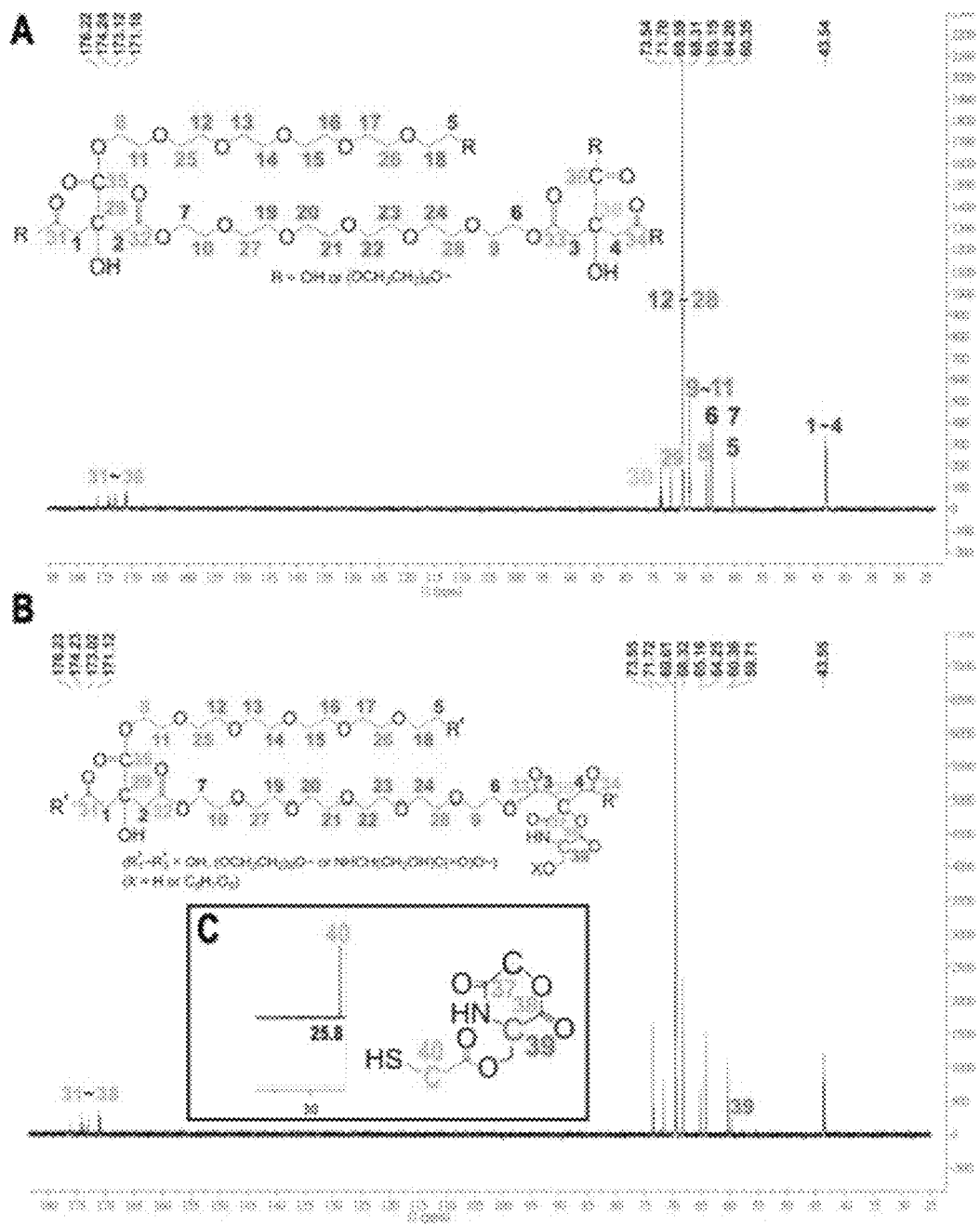
FIGS. 9A-9C are examples of $^{13}$C NMR Characterization of CHPO-Ser oligomers.

For the oligomers without conjugate of serine, the peak about 43 ppm was assigned to carbon which next to central carbon of hexaethlyeneglycol, the peaks of 64, 68 and 69 ppm were —O—$CH_2CH_2$— and —)—$CH_2CH_2$— from hexaethlyeneglycol, 71 and 73 ppm were the central carbon of hexaethlyeneglycol, 170~175 ppm were assigned to carbonyl (C=O) groups from citric acid FIG. 9A(S3-A). On the other hand, there is a clear peak where is located on 59 ppm indicating the carbon 39 of the ring structure FIG. 9B (S3-B). The results demonstrated the presence of a 6-membered ring formed on CHPO-Ser oligomer, which is responsible for the fluorescence property. In addition, the carbon 40 next to —SH present in 25.8 ppm has double confirmed the thiol group conjugated successfully on the oligomer FIG. 9C (S3-C). The number of thiol moieties on the oligomer were confirmed by Ellman's reagent[32], briefly DTNB reacts with free thiol group to release TNB-ions and further ionized to TNB-2, which can be measured at visible light (412 nm) in Tecan plate reader at ambient temperature. The result shows that there were 5~7 SH moieties conjugated on the oligomers. The above characterization confirmed that CHPO-Ser-ET oligomer was successfully synthesized.

Photoluminescent CHPO-Ser-ET-PEG and CHPO-Cys-ET-PEG Hydrogel Fabrication

Figures 2A, 2B, 2C, 2D, 2E, 2F:
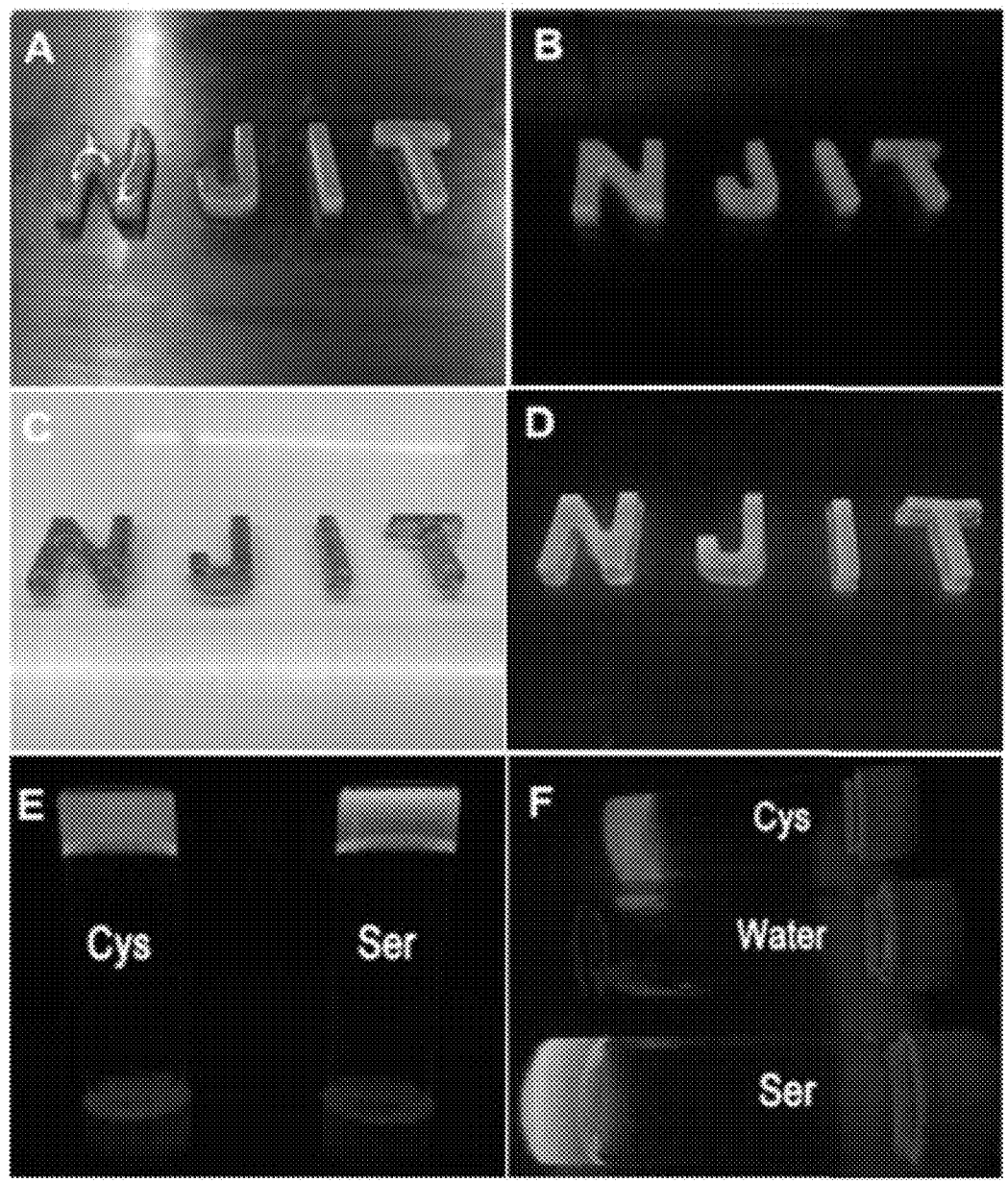
FIGS. 2A-2F illustrate a CHPO-Cys-ET/PEG hydrogel photo image under visible light (A) and photo image under UV light (365 nm) in dark room (B); CHPO-Ser-ET/PEG hydrogel photo image under visible light (C) and under UV light (450 nm) in dark (D); photo image of both CHPO-Cys-ET/PEG hydrogel (blue) and CHPO-Ser-ET/PEG hydrogel (green) in flipped vials under UV light (450 nm) in dark (E); and photo image of both CHPO-Cys-ET/PEG hydrogel (blue), water and CHPO-Ser-ET/PEG hydrogel (green) in tilted vials under UV light (450 nm) in dark (F), where E and F indicate the formation of hydrogel.

To synthesize a photoluminescent hydrogel, both maleimide and acrylate functionalized multi-arm (4 arm or 8 arm) PEG (molecules weight 10 kDa), has been chosen as a cross-linking agent. Gel can be formed through a maleimide-thiol conjugate addition or an acrylate-thiol Michael addition between the self-synthesized photoluminescent oligomers and the above multivalent PEG macromolecules FIG. 1B. First of all, the hydrogels are injectable and moldable as shown in FIGS. 2A and 2C, and show bright photoluminescent properties under 365 and 450 nm excitation wavelength (FIGS. 2B and 2D). In addition, a tilting vial method is also used to prove the formation of photoluminescent hydrogels as shown in FIGS. 2E and 2F (all hydrogels shown in FIG. 2 are 10% weight concentration, PBS=7.4 and in the ambient temperature).

Figures 3A, 3B, 3C, 3D, 3E, 3F:
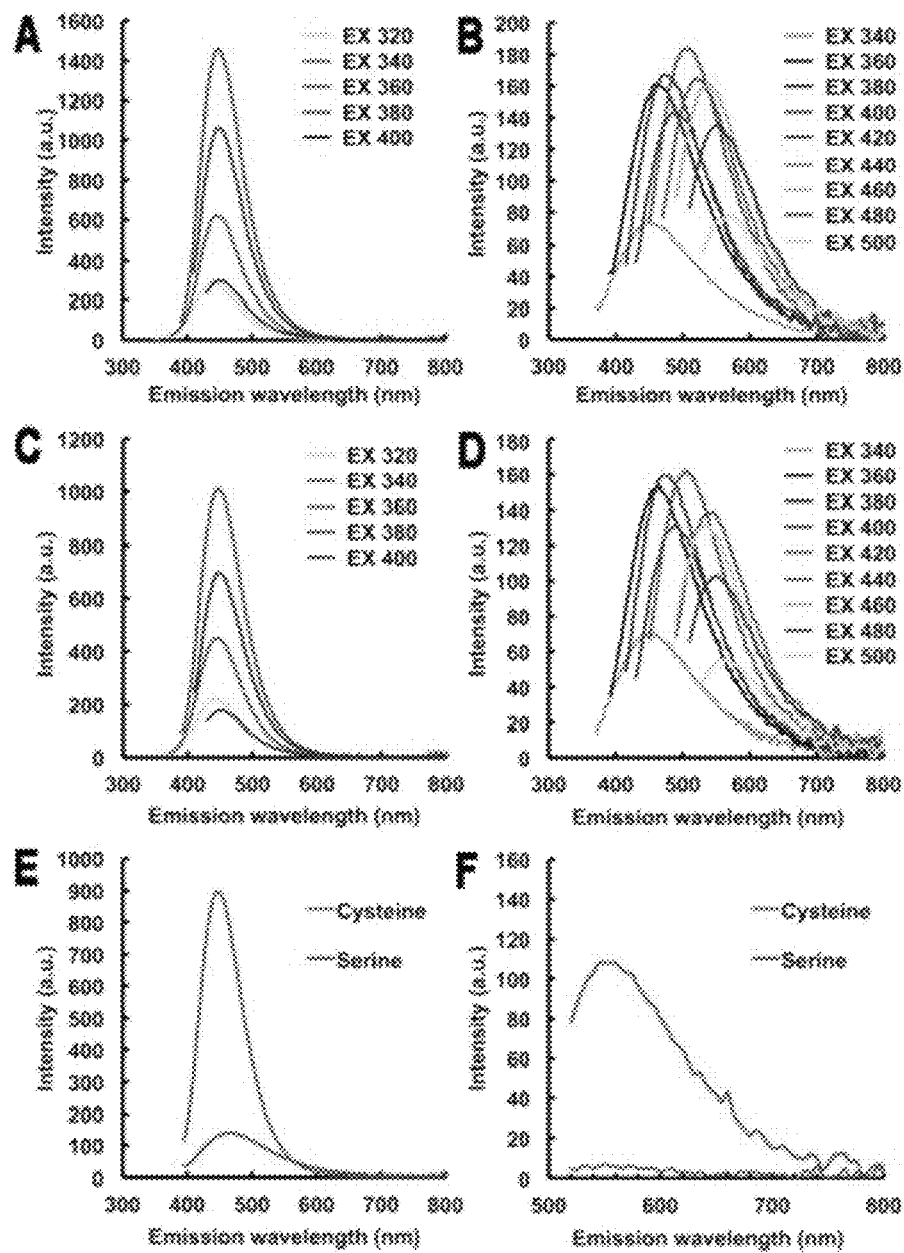
FIG. 3A-3F are diagrams showing fluorescent excitation and emission spectrum characterization, the emission spectra of water solution CHPO-Cys-ET oligomer (A) and CHPO-Ser-ET oligomer (B); and the emission spectra of CHPO-Cys-ET/PEG hydrogel (C) and CHPO-Ser-ET/PEG hydrogel (D); each emission spectral curve correlated with certain excitation wavelength from 200 nm to 800 nm and emission curve was not shown if the intensity is less than 60 a.u; the compared intensity between CHPO-Cys-ET/PEG and CHPO-Ser-ET/PEG hydrogels at fixed excitation of 360 nm (E); the compared intensity between CHPO-Cys-ET/PEG and CHPO-Ser-ET/PEG hydrogels at fixed excitation of 488 nm (F)

Fluorescent Excitation and Emission Spectrum Characterization of CHPO-Ser-ET, CHPO-Cys-ET Oligomers and Hydrogels Intrinsic photoluminescence property of biomaterials is the landmark of future biomedicine applications. It was discovered that both synthesized CHPO-Cys-ET and CHPO-Ser-ET oligomers showed strong emitted fluorescence as well as the hydrogels. The emission spectra of the oligomer solution and its hydrogel are very similar for both CHPO-Cys-ET and CHPO-Ser-ET oligomers. For CHPO-Cys-ET oligomer and hydrogel, the maximum excitation (360 nm) and emission (450 nm) is slightly different from that of CHPO-Ser-ET oligomer and hydrogel, which had maximum excitation and emission wavelengths of 420 nm and 525 nm, respectively FIG. 3A-D. Importantly, the CHPO-Ser-ET solution and hydrogel not only absorb wider wavelengths of light (340-500 nm) than CHPO-Cys-ET (320-400 nm), but also emits fluorescence characteristics under visible light up to 725 nm. CHPO-Ser-ET also emits tunable fluorescent light depending on the excitation wavelength as similar to its hydrogel from 340 to 500 nm (FIGS. 3B and 3D).

Figures 10A, 10B, 10C:
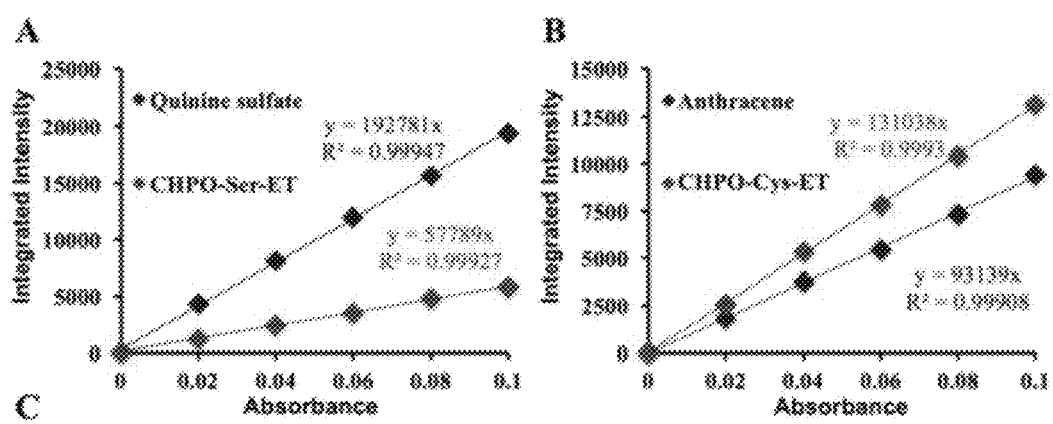
FIGS. 10A-10C illustrate quantum yield of CHPO-Ser-ET and CHPO-Cys-ET.

Additionally, under the same conditions such as concentration and gain among many others, the fluorescence intensity of CHPO-Ser-ET from solution to hydrogel decreased ~10.8% (185 to 165 a.u.) under its maximum excitation wavelength at 420 nm; however, CHPO-Cys-ET hydrogel decreased ~33.3% (1500 to 1000 a.u.) under 365 nm excitation, indicating that the CHPO-Ser-ET/PEG hydrogel has better penetrating property under visible wavelength. It has also been demonstrated that CHPO-Cys-ET/PEG hydrogel has higher emission intensity than that of CHPO-Ser-ET/PEG hydrogel when excited under short wavelength light (365 nm); while CHPO-Ser-ET/PEG hydrogel shows superior light emission intensity at longer excitation wavelength (488 nm) as shown in FIGS. 3E and 3F and the quantum yields of the CHPO-Cys-ET and CHPO-Ser-ET were 36.41 and 16.24% respectively. FIGS. 10a-10C (S4). These results enable the feasibility of non-invasive imaging for monitoring the CHPO-Ser-ET/PEG hydrogel and scaffold degradation and tracking in vivo.

Figures 4A, 4B, 4C, 4D, 4E, 4F, 4G:
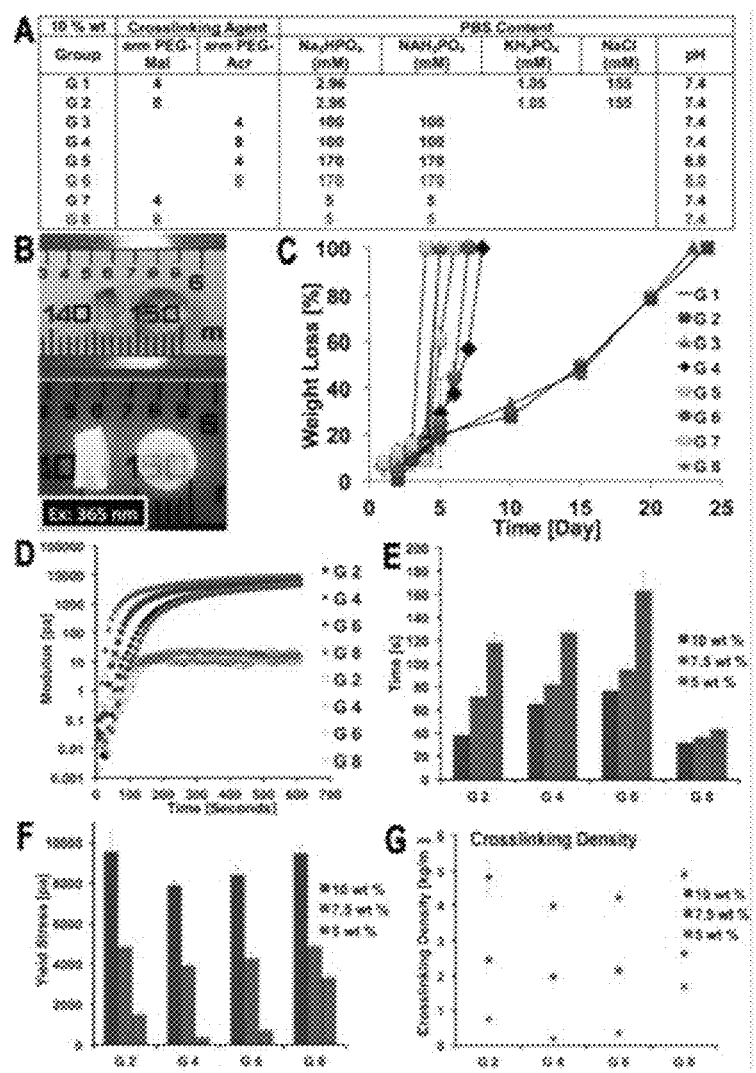
FIGS. 4A-4G illustrate in vitro degradation studies and dynamic rheology of hydrogels, A) variant formulation of CHPO-Ser-ET hydrogel includes different pH, crosslinking agents and PBS contents; B) image of CHPO-Ser-ET hydrogel; (top) without excitation, (bottom) with excitation 450 nm wavelength; C) in vitro degradation of CHPO-Ser-ET hydrogel where shortest and longest degradation were 4 and 25 days respectively; D) dynamic rheology curves at 10 wt %, 37° C. (filled symbols means storage modulus G' and empty symbols means loss modulus G"); E) gelation time as a function of polymer concentration (5, 7.5 and 10%) with varied formulation at 37° C. (For gelation time of rheology test, fifteen seconds were added onto the final gelation time data because of the mixing and performing of the device); F) compared yield stress of different polymer concentration and formulation; and G) crosslinking density with variant formulation, wherein error bars represent mean±standard deviation of mean for n≥3.

Degradation, Mechanical Properties and Drug Release Phenomenon of Photoluminescent Hydro Gels It is important to investigate the relationship between degradation, gel formulations and the physiochemical and mechanical properties of the prepared hydrogel. Hydrogel degradation can be effected by many factors such as porosity, crosslinking density, and polymer concentration among many others[5]. In this study, degradation of various formulation of CHPO-Ser-ET-PEG hydrogels was investigated, as shown in FIG. 4A. Cylinder shape hydrogels were prepared to degradation experiment FIG. 4B (more details discussed herein). All of the formulations of hydrogels have been found to complete degrade within one month, herein, G2 and G8 have longest degradation period ~25 days. There were two different types of degradation phenomenon observed, except G2 and G8 were gradually degraded, others were burst degraded which means the hydrogels crushed at a specific time. For example, G6 only had 40% weight loss at day 6 but it completely degraded at day 7 FIG. 4C. It is probably because of low crosslinking density of hydrogel to lead burst degradation. To be more specific, the chemical bonds break between thiol and maleimde/acrylate, the network system can hold at first; however, at the certain period the whole system cannot embrace and to cause network system destroyed. As such, the mechanical property is the one of major key to effect hydrogel degradation.

To investigate the mechanical property, the DHR III dynamic rheometer was performed. CHPO-Ser-ET oligomer and maleimide/acrylate functionalized multi-arm poly (ethylene glycol) (4-arm or 8-arm, MW10K) were used for hydrogel gelation kinetic and gel strength study. The gelation time was defined by crosslinking points of storage and loss modulus (tan $(\delta)$=G'/G"=1). In this study, various concentration (5~10 wt %), pH, crosslinking agents, temperature and PBS contents has been investigated. Not surprisingly, high polymer concentration gels (10% wt) show superior gel strength and shorter gel formation time compared to 7.5 and 5% weight ratio gel in terms of storage modulus G' and tan $(\delta)$ FIG. 4D-F and FIGS. 11A-11B (S5A, B). In addition, with the introduction of different crosslinking agents, it can lead to distinguish dynamic results of hydrogels. For instance, the gel can be formed immediately when using maleimide as a crosslinking agent compared with the acrylate (~2 minutes) at the same conditions (10 wt %, PBS: $Na_2HPO_4$, $NaH_2PO_4$=170 mM, pH=8). Moreover, at the same conditions (maleimide as a crosslinking agent), when the pH was changed from 7.4 to 8.0, the gelation happened immediately of all the formulations because of in an alkaline environment favors interactions between ions; however, quick gelation often results in weak hydrogel strength probably due to the low cross-linking density.

The content and concentration of PBS will directly affect hydrogel fabrication. When using PBS ($Na_2HPO_4$, $NaH_2PO_4$=5 mM, pH=7.4) the gelation time was ~2 minutes of maleimide as crosslinking agent; nevertheless, increase the PBS concentration to 15 mM the gelation time becomes immediately. It is probably because the release of $H^+$ and $OH^-$ of PBS can assist the ion exchange to accelerate gel formation time[33]. Furthermore, for the same gel composition, gelation at 37° C. is faster than that at low temperature 25° C. due to the increased thiol-maleimide reaction activity at high temperature FIG. 11C(S5C). More importantly, G2 and G8 have better crosslinking density than others FIG. 4G, it correspondence the results of in vitro degradation. Swelling and porosity of hydrogels were also studied FIGS. 12A-12D (S6).

To understand the drug release phenomenon of the hydrogels, varied photoluminescent hydrogels were conducted at 25 and 37° C. respectively. Dextran-NIR fluorescent labeled polymer (6 and 100 kDa) were encapsulated within varied 10 wt % hydrogels. There were three steps of Dextran-NIR released from hydrogels, first of all, both 6 and 100 kDa Dextran-NIR encapsulate within hydrogels released about 20~45% in first 4 hours at 25 and 37° C. FIGS. 13A-13D (S7). The reasons are because a) at first 4 hours, the Dextran-NIR around hydrogels surface was released, in addition, hydrogels starting absorb water and the layer of Dextran-NIR where located next to hydrogels surface was starting dissolved and released from the hydrogels[34] b) next, the system starts to achieve steady stead status and released Dextran-NIR even distribution c) Finally, the burst released of Dextran-NIR has noted due to the degradation of the hydrogels[35]. G2 and G8 has longer release rate than G4 and G6, the results were expectable because of the crosslinking density, porosity and the degradation rate of materials. Above information demonstrated CHPO-Ser-ET-PEG hydrogel, which contains tunable gel formation time, yield strength degradation and drug release rate.

Figures 5A, 5B, 5C, 5D, 5E, 5F, 5G, 5H, 5I, 5J, 5K, 5L:
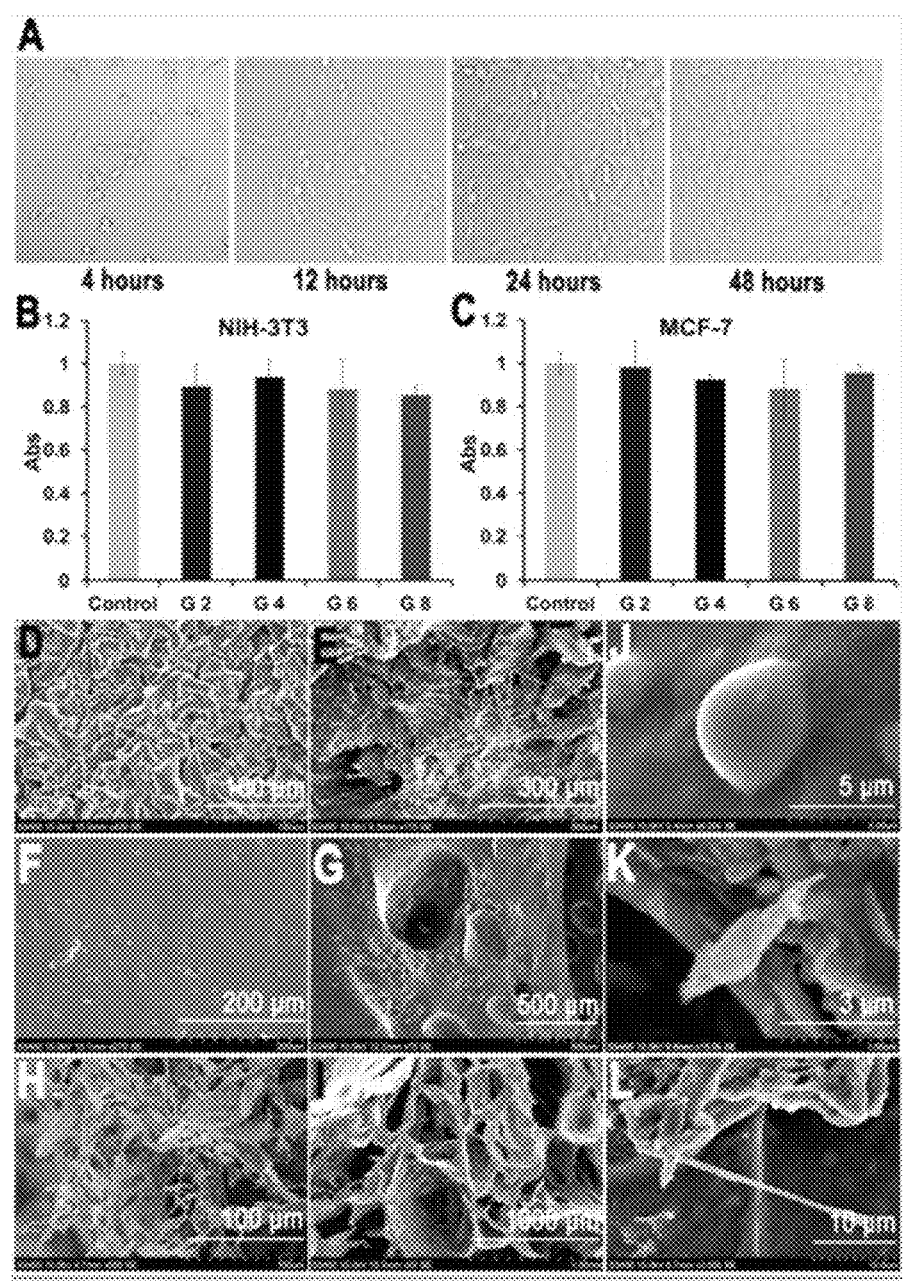
FIGS. 5A-5L illustrate biocompatibility and SEM image of photoluminescent substrate, A) NIH-3T3 attached and proliferated on the CHPO-Ser-ET hydrogel, and after 4 hours, the cell stared to attach on the hydrogel and ~12 hours, cells began to proliferate. XTT assay (Abs=A490$_{nm}$ (Test)-A490$_{nm}$ (Blank)-A660$_{nm}$ (Test)) of B) NIH-3T3 and C) MCF-7 cells shows the significant in vitro biocompatibility of CHPO-Ser-ET hydrogel, wherein control: 96 wells cell culture plate without the hydrogel. D, F & H) surface (E, G & I) and cross section (B, D & F) SEM image of photoluminescent scaffolds G1 (D, E), G2 (F, G) & G6 (H, I), and J, K & L) SEM images of G6 scaffolds seeded with NIH-3T3, wherein error bars represent mean±standard deviation of mean for n≥3.

Cell Adhesion, Biocompatibility and Morphology Studies of Photoluminescence Hydrogels To better understand the biocompatibility of CHPO-Ser-ET-PEG hydrogel, cell adhesion is the one significant factor to determine whether the material is biocompatible or toxic. CGRDS (3.5 mM) was incorporated on the 8 arm PEG-maleimide/acrylate and the results shows superior cell adhesion and proliferation FIG. 5A. Further, XTT assay was used to examine cell viability and proliferation. Both mouse embryonic fibroblast cell (NIH-3T3) and human breast adenocarcinoma cell (MCF-7) were directly contacted with CHPO-Ser-ET hydrogel for 2 days (96 wells cell culture plate with no hydrogel as control). The results show that all formulation with compatible data with control group FIGS. 5B and 5C (few cells were wash out when the hydrogel was removed from 96 wells cell culture plate), indicating that CHPO-Ser-ET based hydrogel contains vitro biocompatibility property.

Morphology is one of significant factor to affect cells migration and proliferation. Many researchers demonstrate that in the 2D culture (surface), cells prefer soften environment to stretch and proliferate[36, 37, 38]. G1, G2 and G6 were investigate in morphology and cell proliferation section. The SEM images of scaffolds surface were presented in FIG. 5D-G1, FIG. 5F-G2 and FIG. 5H-G6, cross sections were presented in FIG. 5E-G1, FIG. 5G-G2 and FIG. 5I-G6. Not surprisingly, G2 has most dense structure, nearly none pores in the surface and this result is predictable due to best cell proliferation in 2D culture and better yield strength from DHR III measurement. However, the cells cannot proliferate in 3D culture of G2 substrate because of dense structure. By contrast, the substrate of G6 has lower yield stress and porous structure to lead perfect environment for 3D culture. The NIH-3T3 cells first attached on the G6 substrate FIG. 5J, next migration FIG. 5K and finally stretch out FIG. 5L. Above information suggests the materials possess three dimensional in vitro biocompatibility properties.

The Photoluminescent Property in Vivo Bioimaging

Figures 6A, 6B, 6C:
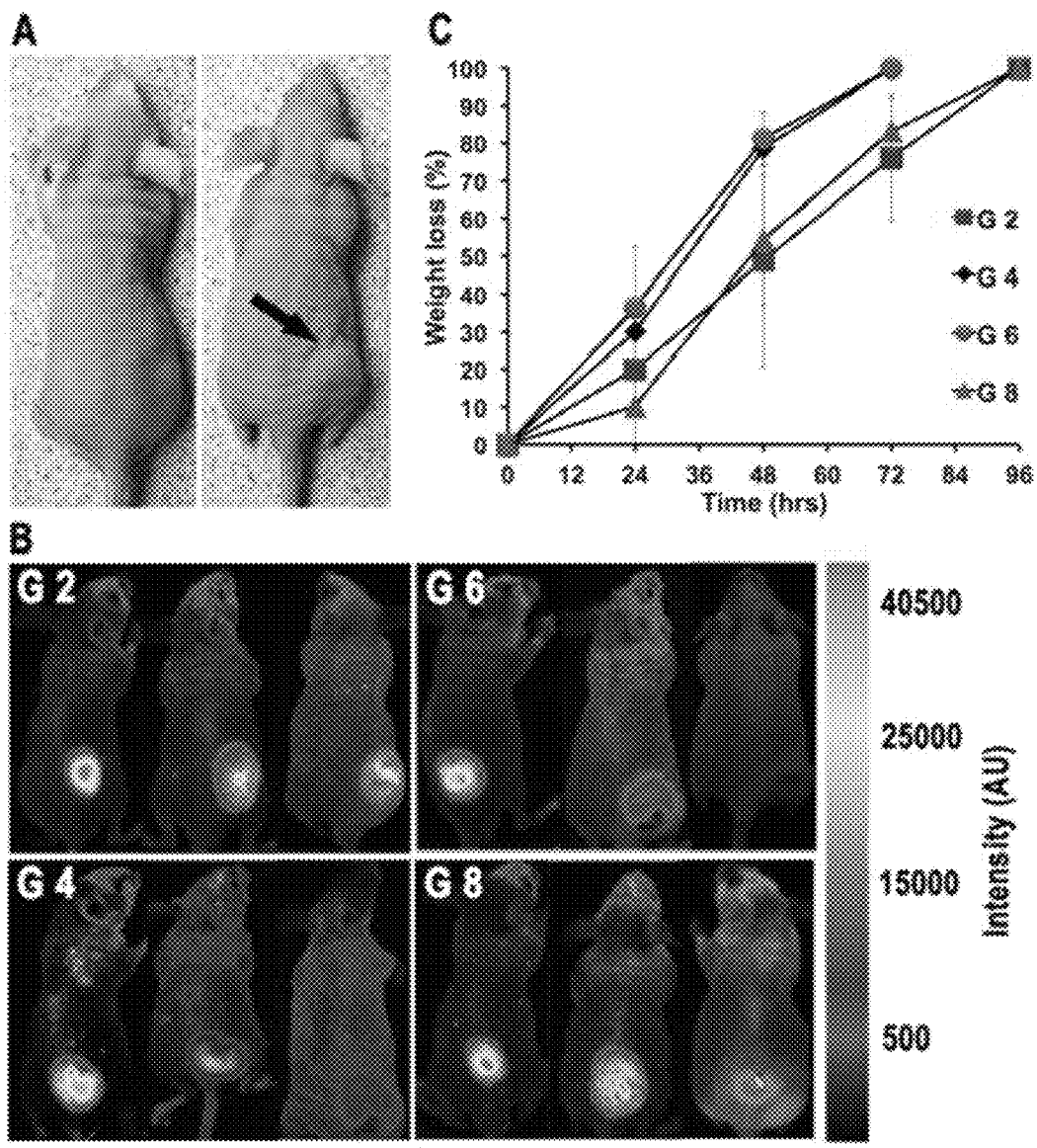
FIGS. 6A-6C illustrate in vivo fluorescence imaging studies, A) nude mice before (left) and after (right) injected CHPO-Ser-ET hydrogel; B) fluorescence images of CHPO-Ser-ET hydrogels injected in a nude mouse from day 1 to day 3 (left to right); and C) degradation of CHPO-Ser-ET based hydrogels, (Exposure time: 3 s), wherein error bars represent mean±standard deviation of mean for n≥3.
Figures 14A, 14B:
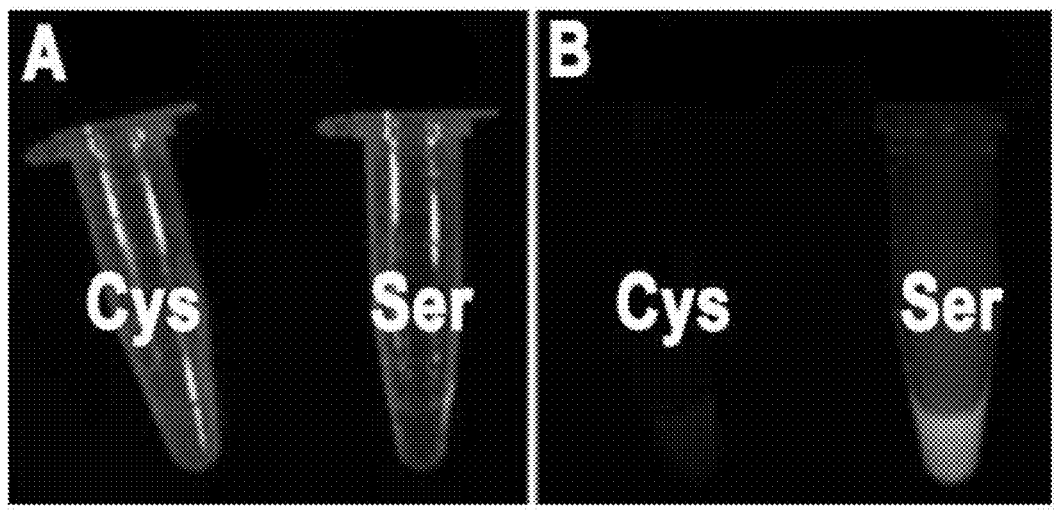
FIGS. 14A-14B illustrate photoluminescent property of CHPO-Ser-ET/PEG and CHPO-Cys-ET/PEG hydrogel.

To test whether the optical property of our synthesized photoluminescent hydrogel would allow in vivo bioimaging and implant tracking, CHPO-Ser-ET/PEG and CHPO-Cys-ET/PEG hydrogel in small test tubes were first examined by using a gel imaging system. Only CHPO-Ser-ET/PEG hydrogel exhibited photoluminescence when exposed to light of wavelengths at 488 nm as shown in FIGS. 14A-14B (S8). Next, the CHPO-Ser-ET/PEG hydrogel was injected beneath the skin, into the nude mouse muscle tissue by using a 22-guage syringe FIG. 6A. The gelation was confirmed by sacrificing the mouse. The CHPO-Ser-ET/PEG hydrogel was readily detected and visualized under 488 nm excitation and 525 nm emission in vivo using a Syngene PXi imaging system (Synoptics Ltd) FIG. 6B. The degradation of hydrogels in nude mice was recorded every 24 hours until no fluorescence was detected. After fluorescence quantitative analysis of hydrogels, G2 and G8 have longer degradation period than G4 and G6 FIG. 6C, the results were expected due to higher yield stress, better crosslinking density and lower % porosity of G2 and G8. More importantly, no fluorescence was detected of all formulation and the gel bump was disappeared within 7 days, indicating the in vivo degradation of the CHPO-Ser-ET/PEG hydrogel. In addition, the CHPO-Ser-ET based hydrogel possess weak fluorescent property under NIR wavelength at exposure time: 3 ms. These results clearly show that CHPO-Ser-ET/PEG hydrogel can be injected in vivo and optically detected and tracked without any fluorescence dye/labeling, suggesting a possibility of using this hydrogel as an implanted scaffold for bioimaging and in vivo material degradation tracking.

A series of hydrogels with intrinsic photoluminescent, biodegradable, biocompatible and injectable properties have been developed. CHPO-Ser-ET and CHPO-Cys-ET based hydrogels possess tunable degradation, gel formation time and yield stress by adjusting the pH, polymer concentration, crosslinking agent, temperature among many others. Different than other materials by using quantum dots, fluorescent proteins and lanthanide chelates, this makes the materials detectable, which remains potential toxicity to cause serious and permanent damage of human or animal bodies. Moreover, our photoluminescence hydrogel has significant biocompatible property in vitro and in vivo due to intrinsic character. Especially CHPO-Ser-ET based hydrogel can be detected under visible light, which brings the breakthrough of biomaterials field. This photoluminescent hydrogel is a new era of biomaterial field. As a result of this study candidate hydrogel formulations have been identified that may find utility as injectable materials for drug release and tissue engineering applications.

Methods: Hydrogel Fabrication

Maleimide or acrylate functionalized multi-arm (4 arm or 8 arm) PEG (molecules weight 10 KDa) as choice for cross-linking agents in this study. Gel can be formed through a maleimide-thiol conjugate addition or an acrylate-thiol Michael addition between our self-synthesized photoluminescent oligomers and the above multivalent PEG macromolecules. Briefly, self-synthesized oligomer CHPO-Ser-ET and 4 or 8 arms PEG-Maleimide/Acrylate (MW 10 KDa) were dissolved individually in PBS to form pre-gel solutions with predetermined weight concentrations. By mixing two solutions, hydrogels can be formed within seconds to hour (depends on formulation) at physiological conditions.

In Vitro Degradation of Hydrogel

Dry hydrogel films were immersed into 48 wells plate with PBS pH=7.4 at 37° C./5% $CO_2$ individually under static conditions and the initial weigh of hydrogels as recorded as $W_a$. PBS will be changed every day to maintain the PH of the solution in 7.4. After certain days (e.g. 1, 3, 5, 7, 21 day), hydrogels were removed from the 48 wells plate, washed by DI water, freeze and lyophilized before weighted. Final hydrogel films were recorded as $W_b$. The degradation of hydrogels as calculated as follows:

Degradation (%)=$[(W_a-W_b)/W_a]*100\%$

Cell Culture, Adhesion and Spreading on the Hydrogel Evaluation

Mouse fibroblast NIH 3T3 (ATCC® CRL-1658) will be cultured in high glucose Dulbecco's Modified Eagle's Medium (DMEM) media containing 10% fetal bovine serum (FBS), 100 units/ml penicillin and 100 μg/ml streptomycin in the incubators maintained at 37° C. with 5% $CO_2$ under fully humidified conditions. Hydrogels were modified by adding CGRDS to improve cell adhesion (Molar ratio at 2:1 between CRGDS and 8 arm PEG-Maleimide). Prior to cell seeding, the hydrogels were immersed in PBS (pH 7.4) for 12 hours, sterilized with 75% ethanol for 1 hour and rinsing with sterile PBS three times to make sure no ethanol remains on the hydrogel. Cells in DMEM will be seeded in a dropwise manner at the density of (7,500 cells/$cm^2$) onto the sterilized hydrogels cast in 96 wells cell culture plate and cultured in a standard protocol. The seeded cells are cultured in the incubators maintained at 37° C. with 5% $CO_2$ and medium was changed daily. Cell morphology (i.e., cell shape and appearance) was observed using a microscope at 6, 12, 18, 24, 36 and 48 hours after cell seeding on the hydrogels.

In Vitro Biocompatibility Studies

NIH-3T3 and MCF-7 cells were observed the biocompatibility of CHPO-Ser-ET hydrogel. After gel fabrication, hydrogel cylindrical samples (~50 μL, diameter=5.6 mm; height=2.9 mm) were immersed in 75% ethanol overnight for sterilization followed by PBS for one day. Cells (density=$5.5*10^4$ cells/$cm^2$) were first placed in 96 wells cell culture plate with cell culture medium. After 6 hours, the hydrogels were placed in 96 wells cell culture plate, which directly contacted with the cells and the cell culture were changed daily. XTT assay was used to examine cell viability and proliferation. After 48 hours, XTT solution was added in 96 wells cell culture plate followed by standard protocols. The plate was then incubated in an incubator at 37° C. with 5% $CO_2$ environment. After specific time, the hydrogels were removed from 96 wells cell culture plate and measured the absorbance of remained cells by plate reader. Cells in 96 well cell culture plate without hydrogels were used as control.

$Abs=A490_{nm}(Test)-A490_{nm}(Blank)-A660_{nm}(Test)$

Morphology of Hydrogel:

Scanning electron microscopy (SEM) is used to observe the morphology of the hydrogel samples. The morphology of hydrogels surface and cross sections are determined after coating the gold in a Sputter Coater. Test samples are blown clean by using compressed air before the SEM test.

In Vivo Bioimage Studies

Balb/c nude mice will be performed in bioimage experiments. First, nude mice anesthetized by isoflurane 1-3% by inhalation and maintained under anesthesia. The precursor solutions 10 wt % will be injected into mice subcutaneous pockets after well mixed (Total volumes of hydrogel precursor solutions are 100 μl and sterilized by 0.22 μm syringe filter). For bioimaging and in vivo degradation studies, PXi gel image system was used for photoluminescent imaging. The images will be taken immediately after hydrogels injected in mice under excitation 488 nm and filter 525 nm. To track the fluorescent intensity of CHOP-Ser-ET hydrogels, the mice will be measured in 12, 24, 48, 72 hours until there is no fluorescent emits from hydrogel bearing mice (n=3).

Statistical Analysis

Samples of each experiment were performed at least three times. Differences between groups of $p \leq 0.05$ were considered statistically significant.

Supplementary Information

The following information is given to further explain and describe the present disclosure. Again, the examples given are merely meant to assist one skilled in the art and not mentioned in any way to limit the disclosure to the embodiments given herein.

Section 1: Symbols and Materials
Section 2 (S1): Oligomers synthesis
Section 3 (S2 & S3): Oligomers characterization includes FTIR, MULDI-TOF, $^1$H and $^{13}$C NMR
Section 4 (S4): Quantum yield analysis
Section 5 (S5, S6 & S7): Dynamic rheology, mechanical properties and drug released measurement of photoluminescent hydrogel
Section 6 (S8): In vitro photoluminescent study Section 1: Symbols and Materials S1.1 Symbols CHPO: Citric acid, hexaethylene glycol photoluminescent oligomer;

CHPO-Ser: Citric acid, hexaethylene glycol photoluminescent oligomer with serine;

CHPO-Cys: Citric acid, hexaethylene glycol photoluminescent oligomer with cysteine;

CHPO-Ser-ET: Citric acid, hexaethylene glycol photoluminescent oligomer with serine and ethyl thioglycolate;

CHPO-Cys-ET: Citric acid, hexaethylene glycol photoluminescent oligomer with cysteine and ethyl thioglycolate;

CHPO-Ser-ET-PEG: Citric acid, hexaethylene glycol photoluminescent oligomer with serine and ethyl thioglycolate with poly ethylene glycol (4 arm PEG-Maleimide (MW: 10,000 g/mole), 8 arm PEG-Maleimide (MW: 10,000 g/mole), 4 arm PEG-Acrylate (MW: 10,000 g/mole) or 8 arm PEG-Acrylate (MW: 10,000 g/mole)) to be crosslinker; and CHPO-Cys-ET-PEG: Citric acid, hexaethylene glycol photoluminescent oligomer with cysteine and ethyl thioglycolate poly ethylene glycol (4 arm PEG-Maleimide (MW: 10,000 g/mole), 8 arm PEG-Maleimide (MW: 10,000 g/mole), 4 arm PEG-Acrylate (MW: 10,000 g/mole) or 8 arm PEG-Acrylate (MW: 10,000 g/mole)) to be crosslinker.

S1.2 Materials

Citric acid, hexaethlyene glycol, L-serine, L-cysteine, ethyl thioglycolate, Lipase B acrylic resin from *Candida antarctica* (CALB), Quinine sulfate, Anthracene and Acetonitrile were purchased from Sigma-Aldrich (St. Louis, Mo., USA). 4 arm PEG-Maleimide (MW: 10,000 g/mole), 8 arm PEG-Maleimide (MW: 10,000 g/mole), 4 arm PEG-Acrylate (MW: 10,000 g/mole), 8 arm PEG-Acrylate (MW: 10,000 g/mole) were purchased from JenKem Technology (Plano, Tex. USA). Dialysis tubes (500~1,000 & 1,000 KDA) were purchased from Spectrum (Houston, Tex. USA). Phosphate buffered saline (PBS), Dulbecco's Modified Eagle's medium (DMEM), Fetal bovine serum (FBS), Penicillin and Mouse fibroblast NIH 3T3 were purchases from American Type Culture Collection (ATCC) (Manassas, Va. 20110 USA). Cell Proliferation Kit (XTT) was purchases from Roche. All chemicals were used as received without any purification.

Section 2: Oligomers Synthesis

S2.1 Synthesis Steps of CHPO-Ser Oligomers

For synthesis of CHPO-Ser: Equimolar amounts of citric acid (1.99 g) and hexaethylene glycol (2.13 g) were added to a 100 mL two-neck round bottom flask for ~180 minutes reaction time at 155° C. under nitrogen protection. The reaction was placed on a magnetic stirrer, followed by the addition of serine (0.22 g) at a molar ratio 1:0.2 between citric acid and serine for an 80 mins reaction time. The oligomers were cool at room temperature before dissolved in DI water, then the products were purified by using a dialysis method (500~1 KD) and followed by freeze dryer for 3 days. The yield of CHPO-Ser oligomers were approach 82%.

S2.2 Enzyme Catalyzed CHPO-Ser Thiolation

To test whether it is possible to introduce multiple valences into the backbone of the amino acids containing CHPO-Ser through an enzyme catalyzed transesterification reaction, *Candida antarctica* Lipase B (CALB) was used as a catalyst to functionalize a thiol containing compound ethyl thioglycolate (ET) to CHPO-Ser. Oligomers were first dissolved in acetonitrile, ethyl thioglycolate and CALB (500 mg) was added in the solution (molar ratio of ethyl thioglycolate and citric acid=2.2:1) at 55~60° C., under magnetic stir and nitrogen protection for 7 hours.

The reaction will stop via filtering out of CALB. The resultant thiol modified oligomers CHPO-Ser-ET was purified through dialysis by using a dialysis tubing (1 K D) and then followed by freeze dryer for 3 days. The yield of CHPO-Ser-ET oligomers were approach 73%.

S2.3 Synthesis of RGD-Functionalized PEG Macromers

CRGDS peptide was used to enhance the cell adhesion of photoluminescent hydrogels. Maleimde/Acrylate-PEG-CRGDS was prepared via a thiol-maleimide and thiol-ene coupling reactions. Briefly, the 8 arm-PEG-Maleimde/Acrylate (10,000 g/mol) and CRGDS with a molar ratio of 1:2 were added in an 8 mL vial and dissolved in PBS with 4 mM and 400 mM triethanolamine (TEA)[1] under nitrogen protection with stirring condition for 90 minutes. The Maleimde/Acrylate-PEG-CRGDS were purified by using a dialysis method (3.5 KD) and then followed by freeze dryer for 3 days. FIG. 7 (S1) shows a schematic illustration of biodegradable photoluminescent (CHPO-Ser-ET) synthesis.

Section 3: Oligomers Characterization

S3.1 Oligomers Characterization of FTIR, MULDI-TOF and $^1$H NMR.

Figures 8A, 8B, 8C, 8D:
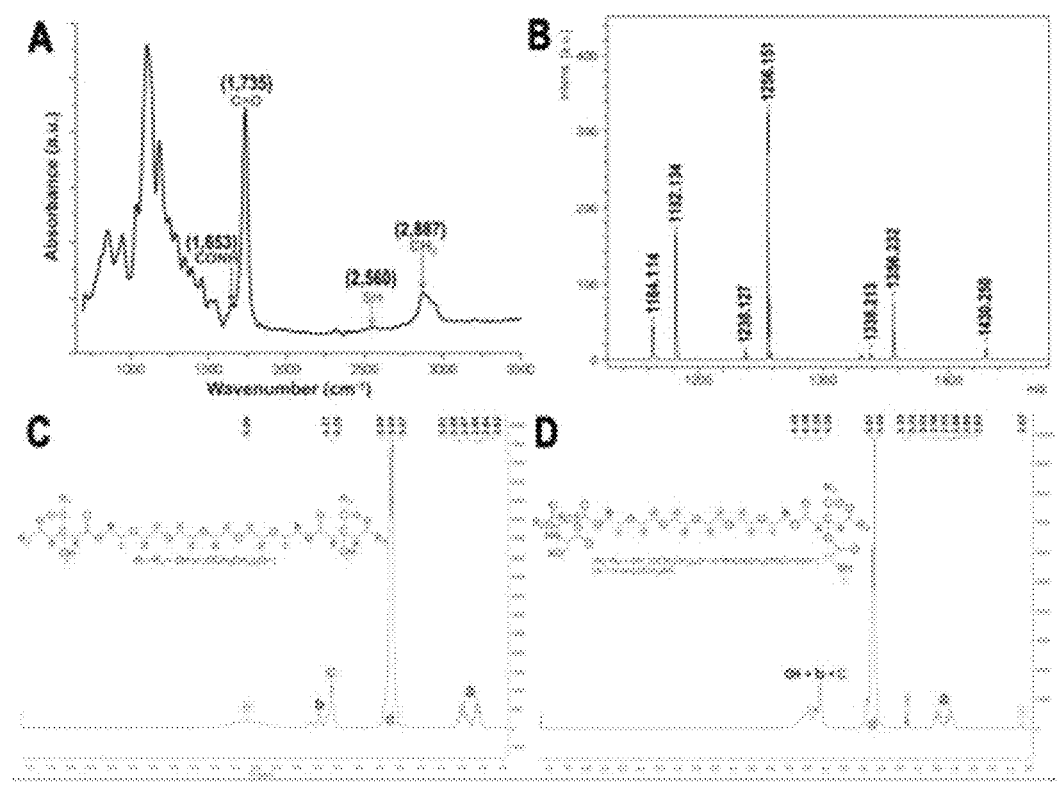
FIGS. 8A-8D are examples of characterization of CHPO-Ser oligomers.

FIGS. 8A-8D (S2) show the characterization of CHPO-Ser oligomers. In FIG. 8A, FTIR spectra of CHPO-Ser-ET. In FIG. 8B, MULDI-TOF spectra of CHPO-Ser-ET. In FIG. 8C, $^1$H NMR spectra of CHPO and D) $^1$H NMR spectra of CHPO-Ser-ET.

S3.2 Oligomers Characterization of $^{13}$C NMR.

FIG. 9A-9C (S3) show $^{13}$C NMR Characterization of CHPO-Ser oligomers. Illustrated in this example are $^{13}$C NMR spectra A) CHPO, B) CHPO-Ser and C) CHPO-Ser-ET.

Section 4: Quantum Yield Analysis

S4.1 Comparative Method of Quantum Yield

To calculate the quantum yield of CHPO-Ser-ET, the comparative method of Williams was performed[2]. Briefly, 10% CHPO-Ser-ET oligomer's solution was prepared. The oligomer's solution was scanned by Tecan infinite plate reader at various excitation wavelengths and the maximal excitation wavelength was determined as the one, which generated the highest emission intensity. Then, measure the absorbance=0, 0.02, 0.04, 0.06, 0.08 and 0.1 at the optimal excitation wavelength of both standard and tested sample. Plot a graph of absorbance versus integrated fluorescence intensity. The fluorescence quantum yield defined as:

$$\varphi_x = \varphi_{ST}(\text{Grad}_x/\text{Grad}_{ST})(\eta_x^2/\eta_{ST}^2)$$

wherein, $\Phi$ is the fluorescence quantum yield, Grad is the gradient obtained from the plot of integrated fluorescence intensity versus absorbance and $\eta$ is the refractive index of the solvent. X and ST denote tested sample and standard respectively. Quinine sulfate as a standard in this experiment and the quantum yield is 54%. Quinine sulfate and Anthracene as a standard in this experiment.

S4.2 Quantum Yield of CHPO-Ser-ET and CHPO-Cys-ET

FIGS. 10A-10C (S4) further illustrate quantum yield of CHPO-Ser-ET and CHPO-Cys-ET.

Plots of integrated fluorescence intensity vs absorbance for example in FIGS. 10A-10C as follows: A) CHPO-Ser-ET with quinine sulfate to be standard, B) CHPO-Cys-ET with anthracene to be standard. C) The compare table of the quantum yield in varying compounds.

Section 5: Dynamic Rheology, Mechanical Properties and Drug Released Measurement S5.1 Dynamic Rheology A DHR-3 Discovery Hybrid Rheometer (TA Instruments, New Castle, Del.) was used to characterize hydrogel gelation kinetics and mechanical properties. Briefly, for each test pre-gel solutions will be sufficiently mixed and a volume of 300 µL is applied to a temperature controlled stage at preset temperature (25 and 37° C.) before the lowering of a 25 mm parallel stainless steel plate to initiate the test. Dynamic time sweep measurements were made within the linear viscoelastic region (strain=5%, angular frequency=1 rad s$^{-1}$). The storage modulus (G') and loss modulus (G") will be recorded as a function of time. The time point where tan ($\delta$)=1 (i.e., G'/G" cross over) will be used to define the gelation time. (The time of loading and mixing have been added in the final gel formation time). The crosslinking density measurements were performed on DHR III. The crosslinking density as define as G'$_R$=vRT$^3$, where v is the number of crosslink sites per unit volume, G is the storage modulus, R is the gas constant and T is the absolute temperature.

Figures 11A, 11B, 11C:
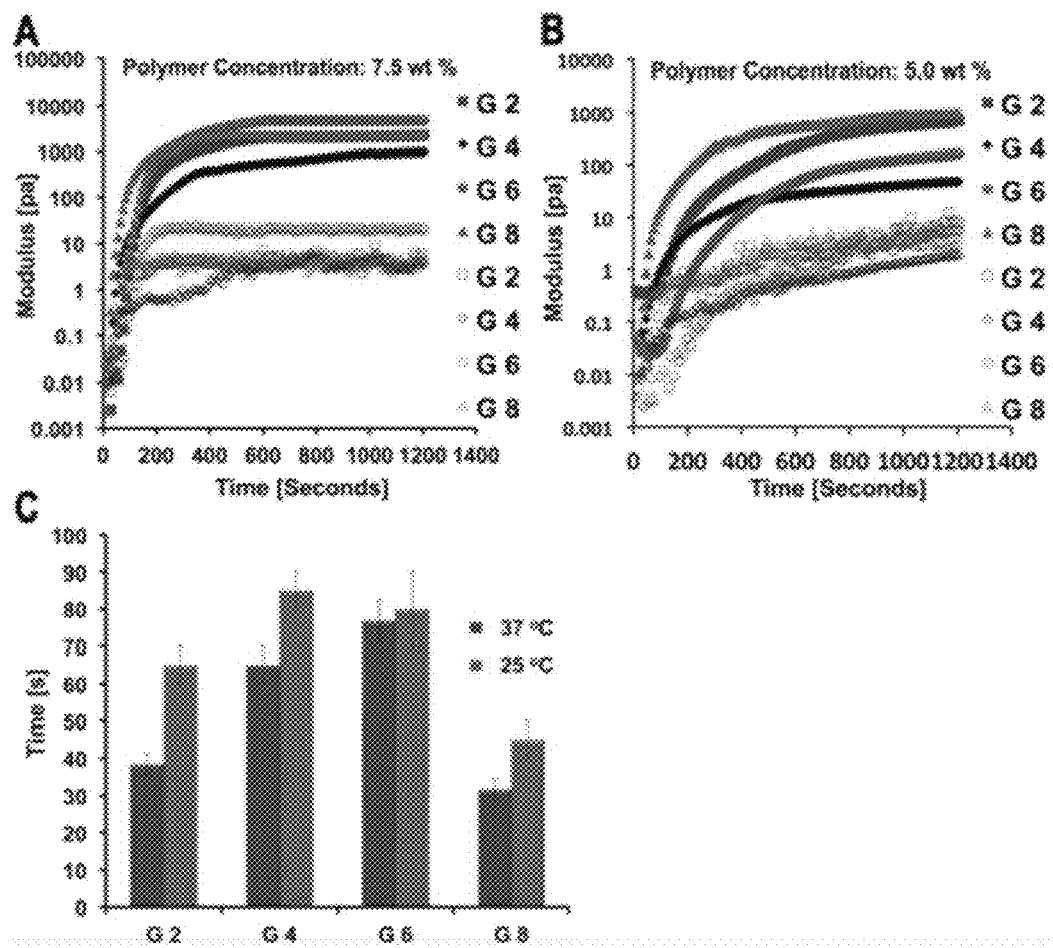
FIGS. 11A-C illustrate the dynamic rheology results with variant concentration and temperature.
Figures 12A, 12B, 12C, 12D:
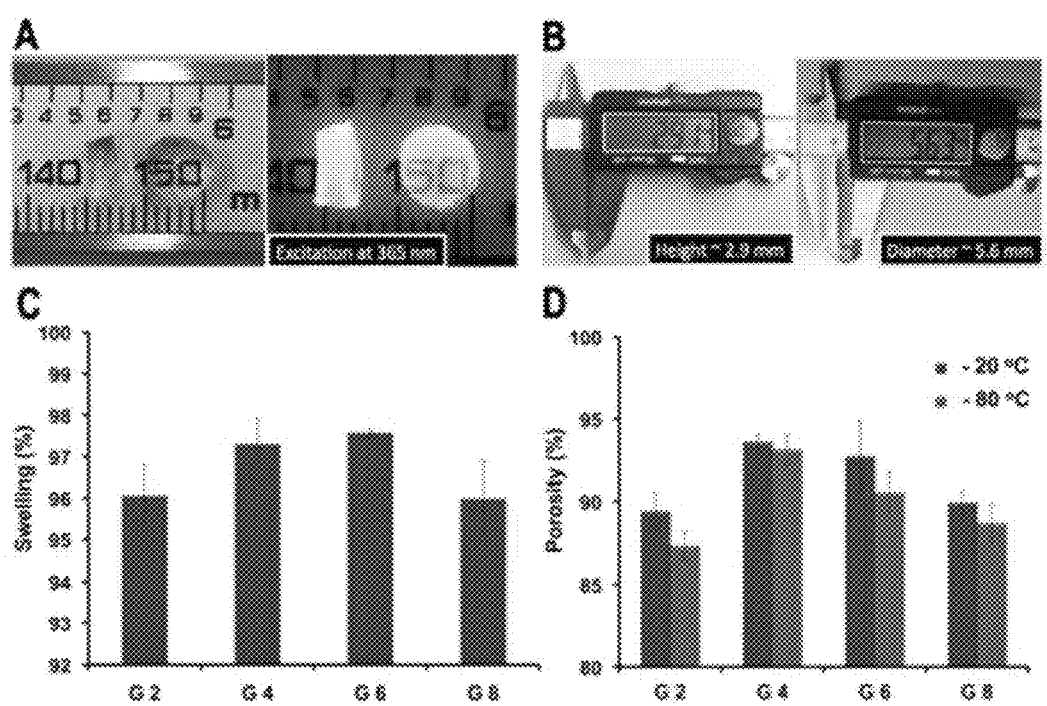
FIGS. 12A-12D illustrate mechanical properties of photoluminescent hydrogel.
Figures 13A, 13B, 13C, 13D:
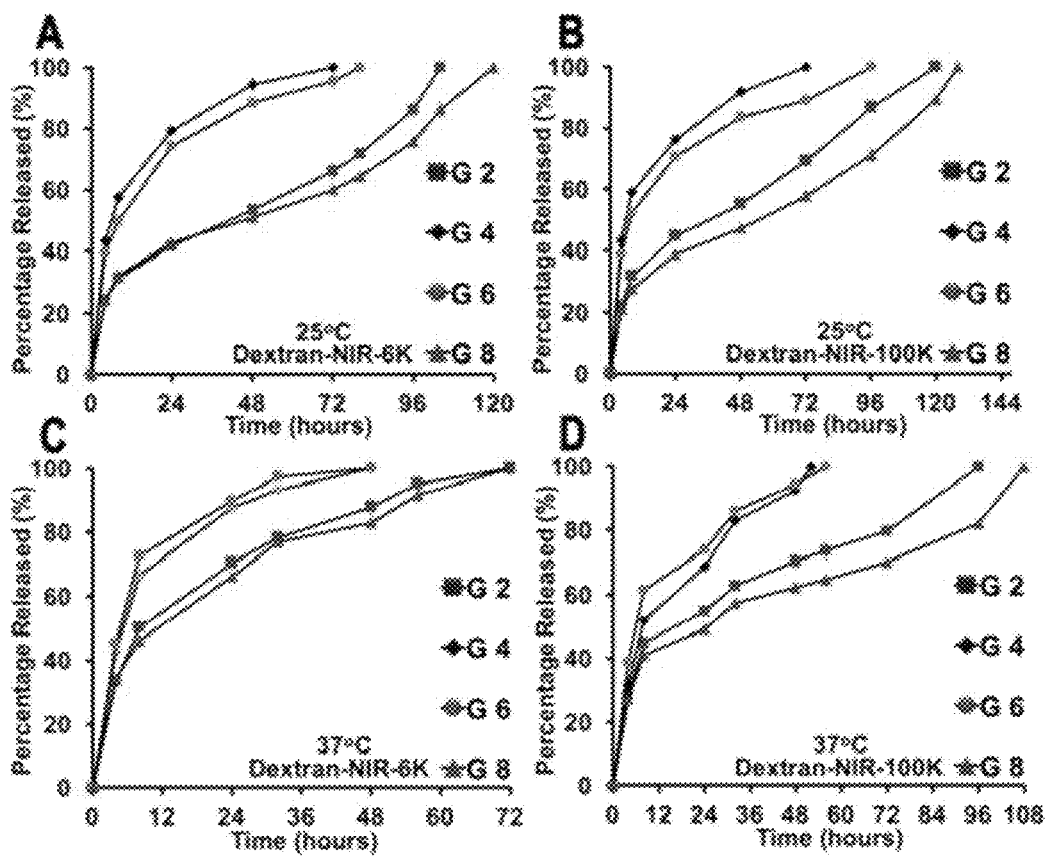
FIGS. 13A-13D illustrate CHPO-Ser-ET/PEG hydrogels released experiments by using Dextran-NIR fluorescent labeled polymer.

FIGS. 11A-11C (S5) show the dynamic rheology results with variant concentration and temperature. Dynamic rheology curves for the curves is FIGS. 11A-11C ae as follows: 7.5 A) and 5.0 B) wt % at 37° C. (Filled symbols means storage modulus G' and empty symbols means loss modulus G"). C) Gelation time with varied formulation at 25 and 37° C. Error bars represent mean±standard deviation of mean for n≥3.

S5.2 Water Content of Hydrogel

After gel fabrication, hydrogel cylindrical samples (~50 µL, diameter=5.6 mm; height=2.9 mm) were immersed in DI water at 37° C. with 5% CO$_2$ for 24 hours to remove unreacted monomers. To obtain the dry weight of the hydrogel, samples were freeze and lyophilized. The weights of hydrogels were recorded as the dry weight (W$_0$) Immersed the dry hydrogel in DI water at 37° C. with 5% CO$_2$ for 24 hours. Removed the hydrogels from the water, use absorbent paper to remove the water of the hydrogel surface and weight the hydrogels as wet weigh (Wi). The water contends of hydrogel as calculated as follows:

$$\text{Water}(\%)=[(W_0-W_i)/W_0]*100\%$$

S5.3 Porosity of Hydrogel

The porosity of the hydrogel samples were measured by the liquid displacement[4]. Briefly, the freeze-dried hydrogel samples were immersed in DI water (volume known, V$_1$) in the beaker for an hour. The total volume (Hydrogels+DI water) as recorded as V$_2$ and the volume of remaining DI water after removed the hydrogel in the beaker was recorded as V$_3$. The porosity (P) of the scaffold was calculated as follows:

$$P(\%)=[(V1-V3)/(V2-V3)]*100\%$$

FIG. 12A-12D (S6) show mechanical properties of photoluminescent hydrogel. The images of the above figures are as follows: A) Images of CHPO-Ser-ET based hydrogel without and with excitation status. B) The dimension of CHPO-Ser-ET based hydrogel. C) Swelling of photoluminescent hydrogels with varied formulation. D) Porosity of varied hydrogels frozen at -20° C. and -80° C. Error bars represent mean±standard deviation of mean for n≥3.

S5.4 Dextran NIR Release Experiment

Two different molecular weights (6 and 100 kDa) of NIR-labeled dextran were conducted of hydrogel permeability experiment at 25 and 37° C. The concentration of Dextran-NIR (500 µg/mL) was encapsulated in CHPL-Ser-ET-PEG hydrogels (Volume ~60 µL). The hydrogels were immersed in 1× PBS at 48 wells cell culture plate and placed in incubator maintained at 37° C. with 5% CO$_2$ (The volume of PBS is 1 mL and changed daily). Fluorescent intensity test was performed by Tecan infinite plate reader at excitation: 754 nm and emission: 783 nm.

FIGS. 13A-13D (S7) show CHPO-Ser-ET/PEG hydrogels released experiments by using Dextran-NIR fluorescent labeled polymer.

Comparison of the cumulative release of varied photoluminescent hydrogels (10% wt) of Dextran-NIR in the above figures as follows: A) 6 kDa, B) 100 kDa at 25° C. and C) 6 kDa, D) 100 kDa at 37° C. Error bars represent mean±standard deviation of mean for n≥3.

Section 6: In Vitro Photoluminescent Study

FIGS. 14A-14B (S8) show photoluminescent property of CHPO-Ser-ET/PEG and CHPO-Cys-ET/PEG hydrogel.

The above figures described the following: A) The images of CHPO-Ser-ET/PEG and CHPO-Cys-ET/PEG hydrogels without excitation source. (Exposure time: 3 ms) B) The images of CHPO-Ser-ET/PEG and CHPO-Cys-ET/PEG hydrogels under 488 nm excitation, 525 nm emission. (Exposure time: 3 s)

While exemplary embodiments have been described herein, it is expressly noted that these embodiments should not be construed as limiting, but rather that additions and modifications to what is expressly described herein also are included within the scope of the invention.

Moreover, it is to be understood that the features of the various embodiments described herein are not mutually exclusive and can exist in various combinations and permutations, even if such combinations or permutations are not made express herein, without departing from the spirit and scope of the invention.

REFERENCES

1. Perale G, Rossi F, Sundstrom E, Bacchiega S, Masi M, Forloni G, et al. Hydrogels in spinal cord injury repair strategies. *ACS chemical neuroscience* 2011, 2(7): 336-345.
2. Slaughter B V, Khurshid S S, Fisher O Z, Khademhosseini A, Peppas N A. Hydrogels in regenerative medicine. *Adv Mater* 2009, 21(32-33): 3307-3329.
3. Yu L, Ding J. Injectable hydrogels as unique biomedical materials. *Chemical Society reviews* 2008, 37(8): 1473-1481.
4. Seliktar D. Designing cell-compatible hydrogels for biomedical applications. *Science* 2012, 336(6085): 1124-1128.
5. Tsou Y-H, Khoneisser J, Huang P-C, Xu X. Hydrogel as a bioactive material to regulate stem cell fate. *Bioactive Materials* 2016.
6. Jeong B, Bae Y H, Lee D S, Kim S W. Biodegradable block copolymers as injectable drug-delivery systems. *Nature* 1997, 388(6645): 860-862.
7. Wang C, Varshney R R, Wang D A. Therapeutic cell delivery and fate control in hydrogels and hydrogel hybrids. *Advanced drug delivery reviews* 2010, 62(7-8): 699-710.
8. Watson B M, Vo T N, Tatara A M, Shah S R, Scott D W, Engel P S, et al. Biodegradable, phosphate-containing, dual-gelling macromers for cellular delivery in bone tissue engineering. *Biomaterials* 2015, 67: 286-296.
9. Ren K, He C, Xiao C, Li G, Chen X. Injectable glycopolypeptide hydrogels as biomimetic scaffolds for cartilage tissue engineering. *Biomaterials* 2015, 51: 238-249.
10. Kwon J S, Kim S W, Kwon D Y, Park S H, Son A R, Kim J H, et al. In vivo osteogenic differentiation of human turbinate mesenchymal stem cells in an injectable in situ-forming hydrogel. *Biomaterials* 2014, 35(20): 5337-5346.
11. Vo T N, Kasper F K, Mikos A G. Strategies for controlled delivery of growth factors and cells for bone regeneration. *Advanced drug delivery reviews* 2012, 64(12): 1292-1309.
12. Li Y, Rodrigues J, Tomas H. Injectable and biodegradable hydrogels: gelation, biodegradation and biomedical applications. *Chemical Society reviews* 2012, 41(6): 2193-2221.
13. Elisseeff J, McIntosh W, Anseth K, Riley S, Ragan P, Langer R. Photoencapsulation of chondrocytes in poly (ethylene oxide)-based semi-interpenetrating networks. *Journal of biomedical materials research* 2000, 51(2): 164-171.
14. Kretlow J D, Young S, Klouda L, Wong M, Mikos AG. Injectable biomaterials for regenerating complex craniofacial tissues. *Adv Mater* 2009, 21(32-33): 3368-3393.
15. Ghobril C, Grinstaff M W. The chemistry and engineering of polymeric hydrogel adhesives for wound closure: a tutorial. *Chemical Society reviews* 2015, 44(7): 1820-1835.
16. Artzi N, Oliva N, Puron C, shireet S, Artzi S, bon Ramos A, et al. In vivo and in vitro tracking of erosion in biodegradable materials using non-invasive fluorescence imaging. *Nature materials* 2011, 10(9): 704-709.
17. Kim S H, Lee J H, Hyun H, Ashitate Y, Park G, Robichaud K, et al. Near-infrared fluorescence imaging for noninvasive trafficking of scaffold degradation. *Scientific reports* 2013, 3: 1198.
18. Li J, Hong X, Liu Y, Li D, Wang Y W, Li J H, et al. Highly Photoluminescent CdTe/Poly(N-isopropylacrylamide) Temperature-Sensitive Gels. *Advanced Materials* 2005, 17(2): 163-166.
19. Wang Z, Zhang Y, Zhang J, Huang L, Liu J, Li Y, et al. Exploring natural silk protein sericin for regenerative medicine: an injectable, photoluminescent, cell-adhesive 3D hydrogel. *Scientific reports* 2014, 4: 7064.
20. Zhang Y, Liu J, Huang L, Wang Z, Wang L. Design and performance of a sericin-alginate interpenetrating network hydrogel for cell and drug delivery. *Scientific reports* 2015, 5: 12374.
21. Berdichevski A, Simaan Yameen H, Dafni H, Neeman M, Seliktar D. Using bimodal MRI/fluorescence imaging to identify host angiogenic response to implants. *Proceedings of the National Academy of Sciences of the United States of America* 2015, 112(16): 5147-5152.
22. Breul A M, Hager M D, Schubert US. Fluorescent monomers as building blocks for dye labeled polymers: synthesis and application in energy conversion, biolabeling and sensors. *Chemical Society reviews* 2013, 42(12): 5366-5407.
23. Wang M X, Yang C H, Liu Z Q, Zhou J, Xu F, Suo Z, et al. Tough photoluminescent hydrogels doped with lanthanide. *Macromolecular rapid communications* 2015, 36(5): 465-471.
24. Bunzli J C, Piguet C. Taking advantage of luminescent lanthanide ions. *Chemical Society reviews* 2005, 34(12): 1048-1077.
25. Jaiswal J K, Mattoussi H, Mauro J M, Simon S M. Long-term multiple color imaging of live cells using quantum dot bioconjugates. *Nature biotechnology* 2003, 21(1): 47-51.
26. Zhang Y, Tran R T, Qattan I S, Tsai Y T, Tang L, Liu C, et al. Fluorescence imaging enabled urethane-doped citrate-based biodegradable elastomers. *Biomaterials* 2013, 34(16): 4048-4056.
27. Hardman R. A toxicologic review of quantum dots: toxicity depends on physicochemical and environmental factors. *Environmental health perspectives* 2006, 114(2): 165-172.
28. Montgomery C P, Murray B S, New E J, Pal R, Parker D. Cell-penetrating metal complex optical probes: targeted and responsive systems based on lanthanide luminescence. *Accounts of chemical research* 2009, 42(7): 925-937.
29. Yang J, Zhang Y, Gautam S, Liu L, Dey J, Chen W, et al. Development of aliphatic biodegradable photoluminescent polymers. *Proceedings of the National Academy of Sciences of the United States of America* 2009, 106(25): 10086-10091.
30. Xie Z, Zhang Y, Liu L, Weng H, Mason R P, Tang L, et al. Development of intrinsically photoluminescent and photostable polylactones. *Adv Mater* 2014, 26(26): 4491-4496.
31. Gyawali D, Zhou S, Tran R T, Zhang Y, Liu C, Bai X, et al. Fluorescence imaging enabled biodegradable photostable polymeric micelles. *Advanced healthcare materials* 2014, 3(2): 182-186.
32. Bowman G R, Bolin E R, Hart K M, Maguire B C, Marqusee S. Discovery of multiple hidden allosteric sites by combining Markov state models and experiments. *Proceedings of the National Academy of Sciences of the United States of America* 2015, 112(9): 2734-2739.
33. Jiang J. Gelation Time and Rheological Property of Gelatin Gels Prepared with a Phosphate-buffered Saline-ethanol Solution. Case Western Reserve University, 2015.
34. Gupta P, Vermani K, Garg S. Hydrogels: from controlled release to pH-responsive drug delivery. *Drug Discov Today* 2002, 7(10): 569-579.
35. Hoffman A S. Hydrogels for biomedical applications. *Adv Drug Deliv Rev* 2012, 64: 18-23.
36. Discher D E, Janmey P, Wang Y L. Tissue cells feel and respond to the stiffness of their substrate. *Science* 2005, 310(5751): 1139-1143.
37. Murphy W L, McDevitt T C, Engler A J. Materials as stem cell regulators. *Nature materials* 2014, 13(6): 547-557.
38. Thiele J, Ma Y, Bruekers S M, Ma S, Huck W T. 25th anniversary article: Designer hydrogels for cell cultures: a materials selection guide. *Adv Mater* 2014, 26(1): 125-147.

SUPPLEMENTARY REFERENCES

1. Phelps E A, Enemchukwu N O, Fiore V F, Sy J C, Murthy N, Sulchek T A, et al. Maleimide cross-linked bioactive PEG hydrogel exhibits improved reaction kinetics and cross-linking for cell encapsulation and in situ delivery. *Adv Mater* 2012, 24(1): 64-70, 62.
2. Williams A T R, Winfield S A, Miller J N. Relative fluorescence quantum yields using a computer-controlled luminescence spectrometer. *Analyst* 1983, 108(1290): 1067-1071.

3. Jiang H, Su W, Mather P, Bunning T. Rheology of highly swollen chitosan/polyacrylate hydrogels. *Polymer* 1999, 40(16): 4593-4602.
4. Wang Z, Zhang Y, Zhang J, Huang L, Liu J, Li Y, et al. Exploring natural silk protein sericin for regenerative medicine: an injectable, photoluminescent, cell-adhesive 3D hydrogel. *Scientific reports* 2014, 4: 7064.

What is claimed is:

1. A photoluminescent dopant-free hydrogel having biodegradable properties, comprising:
    a dopant-free polyester-based biodegradable photoluminescent hydrogel defined as a citric acid and hexaethylene glycol based polyester oligomer-serine-ethyl thioglycolate-polyethylene glycol (CHPO-Ser-ET-PEG) hydrogel, the hydrogel is synthesized by:
    (1) synthesizing a fluorescent oligomer from reacting an amino acid Serine (Ser), a citric acid, and a hexaethylene glycol to form a citric acid and hexaethylene glycol serine based polyester oligomer (CHPO-Ser), followed by a transesterification reaction with a *Candida antarctica* Lipase B (CALB) first catalyst to functionalize a thiol containing compound ethyl thioglycolate (ET) to the citric acid and the hexaethylene glycol serine based polyester oligomer (CHPO-Ser),
    the fluorescent oligomer has at least 5 to 7 thiol groups singularly conjugated thereon through the CALB catalyzed transesterification reaction; and
    (2) reacting the oligomer with a multiple arm polyethylene glycol (PEG) second catalyst to form the hydrogel; and
    wherein the hydrogel emits a fluorescence under visible light excitation with emissions up to 720 nm.

2. The photoluminescent hydrogel of claim 1, wherein the multiple arm polyethylene glycol (PEG) second catalyst further includes a maleimide crosslinking agent.

3. The photoluminescent hydrogel of claim 1, wherein addition of Serine (Ser) is at a molar ratio of 1:0.2 between citric acid and serine (Ser).

4. The photoluminescent hydrogel of claim 3, wherein the CHPO-Ser-ET/PEG hydrogel is an injectable hydrogel individually that emits the fluorescence under visible light excitation and completely degrades over time.

5. The photoluminescent hydrogel of claim 4, wherein the CHPO-Ser-ET/PEG hydrogel is an injectable CHPO-Ser-ET/PEG hydrogel that emits fluorescence at excitation of about 488 nm, and an emission of about 525 nm.

6. The photoluminescent hydrogel of claim 1, wherein the hydrogel functions as both an injectable scaffold and a fluorescent imaging probe with a chemical property that avoids carcinogenesis and toxicity associated with fluorescent dopants.

* * * * *